US006969587B2

(12) United States Patent
Taylor

(10) Patent No.: US 6,969,587 B2
(45) Date of Patent: Nov. 29, 2005

(54) DETECTION OF NUCLEIC ACID HETERODUPLEX MOLECULES BY ANION-EXCHANGE CHROMATOGRAPHY

(76) Inventor: Paul D. Taylor, 775 W. 8th St., Gilroy, CA (US) 95020

( * ) Notice: Subject to any disclaimer, the term of this patent is extended or adjusted under 35 U.S.C. 154(b) by 563 days.

(21) Appl. No.: 09/756,070

(22) Filed: Jan. 6, 2001

(65) Prior Publication Data

US 2002/0164589 A1 Nov. 7, 2002

Related U.S. Application Data

(63) Continuation-in-part of application No. 09/687,834, filed on Oct. 11, 2000, now abandoned.
(60) Provisional application No. 60/194,652, filed on Apr. 4, 2000.

(51) Int. Cl.$^7$ .......................... C12Q 1/68; C12N 15/00; C12N 15/63; C12N 1/20; C07H 21/04

(52) U.S. Cl. ..................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1

(58) Field of Search .......................... 435/6, 7.1, 91.2, 435/91.1; 436/63, 94, 501, 518; 536/23.1, 24.31, 24.32, 24.33, 24.3; 210/656; 935/6

(56) References Cited

U.S. PATENT DOCUMENTS

| 4,936,974 A | 6/1990 | Rose et al. |
| 4,959,176 A | 9/1990 | Slocum et al. |
| 5,506,103 A * | 4/1996 | Cohen et al. .................. 435/6 |
| 5,585,236 A | 12/1996 | Bonn et al. |
| 5,624,798 A | 4/1997 | Yamamoto et al. |
| 5,633,129 A | 5/1997 | Karger et al. |
| 5,795,976 A | 8/1998 | Oefner et al. |
| 5,801,237 A | 9/1998 | Johansson |
| 5,856,192 A | 1/1999 | Bloch |
| 5,866,429 A | 2/1999 | Bloch |
| 6,265,168 B1 | 7/2001 | Gjerde et al. |
| 6,287,822 B1 | 9/2001 | Gjerde et al. |
| 6,306,592 B1 * | 10/2001 | Bertling .......................... 435/6 |

FOREIGN PATENT DOCUMENTS

| EP | 0 507 591 A2 | 10/1992 |
| EP | 0 270 017 A2 | 6/1998 |
| WO | WO 91/00145 | 1/1991 |
| WO | WO 97/19347 | 5/1997 |
| WO | WO 00/50759 | 8/2000 |
| WO | WO 01/27331 | 4/2001 |

OTHER PUBLICATIONS

Ausserer, W., et al., BioTechniques, 19:1 pp 136–139 (1995).
Bio–Rad Chromatography: The History Behind UNO, pp. 1–8 (downloaded Apr. 20, 2000).
Bio–Rad Chromatography—Biochromatography Columns, Nucleotide and Oligonucleotide Separations on an UNO Q1 Ion Exchange Column, 4 pages.
Brownlee, R.G., et al., Journal of Chromatography, 533:87–96 (1990).
Colpan, M., et al., Journal of Chromatography, 296:339–353 (1984).
Drager et al. High–Performance Anion–Exchange Chromatpgraphy of Oligonucleotides, Analytical Biochemistry, 145:47–56 (1985).
Ellegren, H., et al., Journal of Chromatography, 467:217–226 (1989).
Eriksson et al. Separation of DNA Restriction Fragments by Ion–Pair Chromatography, Journal of Chromatography, 359:265–274 (1986).
Haupt, W., et al., Comparison of Several High–Performance Liquid Chromatography Techniques for the Separation of Oligodeoxynucleotides According to their Chain Lenghts, Journal of Chromatography, 260:419–427 (1983).
Huber et al., A Comparison of Micropellicular Anion–Exchange and Reversed–Phase Stationary Phases for HPLC Analysis of Oligonucleotides, LC–GC 14:114–127 (1996).
Kato et al. Separation of DNA Restriction Fragments by High–Performance Ion–Exchange Chromatography on a Non–Porous Ion Exchanger, Journal of Chromatography, 478: 264–268 (1989).
Kleymenova, E., et al., Application of High–Preformance Liquid Chromatography–Based Analysis of DNA Fragments to Molecular Carcinogenesis, Molecular Carcinogenesis, 29:51–58 (2000).
Li, J., et al., Novel Polymeric Resins for Anion–Exchange Chromatography, Journal of Chromatography A, 793:231–238 (1998).
Lloyd et al., Analysis of DNA and Degradation Products Using a Polymeric Strong Anion Exchanger, 8th International Symposium of HPLC of Proteins, Peptides and Polynucleotides Copenhagen, Denmark, 10/31–11/2 (1988).
Lloyd, L., et al., Oligonucleotide Analysis by Anion Exchange HPLC, Bioseparation, 2:207–215 (1991).

(Continued)

Primary Examiner—Jeffrey Fredman
Assistant Examiner—Arun Chakrabarti

(57) ABSTRACT

The present invention describes a method for separating or partially separating heteroduplex and homoduplex DNA molecules in a mixture. In the method, the mixture is applied to an anion-exchange chromatography medium. The heteroduplex and homoduplex molecules are eluted with a mobile phase containing an eluting salt, including an anion and a cation, a buffer, and preferably including an organic solvent. The eluting is carried out under conditions effective to at least partially denature the heteroduplexes (e.g., thermal or chemical denaturing) resulting in the separation of the heteroduplexes from the homoduplexes. The method has many applications including, but not limited to, detecting mutations and comparative DNA sequencing.

45 Claims, 1 Drawing Sheet

OTHER PUBLICATIONS

Maa et al, Rapid High–Performance Liquid Chromatography of Ncleic Acids with Polystyrene–Based Micropellicular Anion Exchangers, Journal of Chromatography, 508:61–73 (1990).

McLaughlin, L.W., et al., Mixed–Mode Chromatography of Nucleic Acids, Chem. Rev. 89:309–319 (1989).

Mhatre et al., Interfacing Gradient Elution Ion–Exchange Chromatography (IEC) and Low Angle Laser Light Scattering Photometry (LALLS) for Analysis of Proteins, J. Chromatography, Submitted for Publication Jul., 1991.

Ohmiya, Y., et al., Separation of DNA Fragments by High–Resolution Ion–Exchange Chromatography on a Nonporous QA Column, Analytical Biochemistry, 189:126–130 (1990).

Scholten, A., et al., Journal of Chromatography, 218:3–13 (1981).

Van Vliet, H. P., et al., Journal of Chromatography, 363:187–198 (1986).

Weber, A. J., et al., Anal. Chem., 59:1452–1457 (1987).

* cited by examiner

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: Primer

<400> SEQUENCE: 1
aggcactggt cagaatgaag                20

<210> SEQ ID NO 2
<211> LENGTH: 20
<212> TYPE: DNA
<213> ORGANISM: Artificial Sequence
<220> FEATURE:
<221> NAME/KEY: primer_bind
<222> LOCATION: (190)...(209)

```
<223> OTHER INFORMATION: Primer

<400> SEQUENCE: 2
aatggaaaat acagctcccc                                              20

<210> SEQ ID NO 3
<211> LENGTH: 209
<212> TYPE: DNA
<213> ORGANISM: Homo sapiens
<220> FEATURE:
<221> NAME/KEY: STS
<222> LOCATION: (1)...(209)
<223> OTHER INFORMATION: sY81

<400> SEQUENCE: 3
aggcactggt cagaatgaag tgaatggcac acaggacaag tccagaccca ggaaggtcca    60
gtaacatggg agaagaacgg aaggagttct aaaattcagg gctcccttgg gctcccctgt   120
ttaaaaatgt aggttttatt attatatttc attgttaaca aaagtccatg agatctgtgg   180
aggataaagg gggagctgta ttttccatt                                     209

<210> SEQ ID NO 4
<211> LENGTH: 209
<212> TYPE: DNA
<213> ORGANISM: Homo sapiens
<220> FEATURE:
<221> NAME/KEY: STS
<222> LOCATION: (1)...(209)
<223> OTHER INFORMATION: sY81

<400> SEQUENCE: 4
aggcactggt cagaatgaag tgaatggcac acaggacaag tccagaccca ggaaggtcca    60
gtaacatggg agaagaacgg aaggagttct aaaattcagg gctcccttgg gctcccctgt   120
ttaaaaatgt aggttttatt attatatttc attgttaaca aaagtccgtg agatctgtgg   180
aggataaagg gggagctgta ttttccatt                                     209

<210> SEQ ID NO 5
<211> LENGTH: 209
<212> TYPE: DNA
<213> ORGANISM: Homo sapiens
<220> FEATURE:
<221> NAME/KEY: STS
<222> LOCATION: (1)...(209)
<223> OTHER INFORMATION: sY81

<400> SEQUENCE: 5
aatggaaaat acagctcccc ctttatcctc cacagatctc atggactttt gttaacaatg    60
aaatataata ataaaaccta cattttaaa caggggagcc caagggagcc ctgaatttta   120
gaactccttc cgttcttctc ccatgttact ggaccttcct gggtctggac ttgtcctgtg   180
tgccattcac ttcattctga ccagtgcct                                     209

<210> SEQ ID NO 6
<211> LENGTH: 209
<212> TYPE: DNA
<213> ORGANISM: Homo sapiens
<220> FEATURE:
<221> NAME/KEY: STS
<222> LOCATION: (1)...(209)
<223> OTHER INFORMATION: sY81

<400> SEQUENCE: 6
aatggaaaat acagctcccc ctttatcctc cacagatctc acggactttt gttaacaatg    60
```

```
aaatataata ataaaaccta catttttaaa caggggagcc caagggagcc ctgaatttta      120
gaactccttc cgttcttctc ccatgttact ggaccttcct gggtctggac ttgtcctgtg      180
tgccattcac ttcattctga ccagtgcct                                        209
```

DETECTION OF NUCLEIC ACID HETERODUPLEX MOLECULES BY ANION-EXCHANGE CHROMATOGRAPHY

CROSS REFERENCE TO RELATED CO-PENDING APPLICATIONS

This application is a continuation-in-part or U.S. patent application Ser. No. 09/687,834 filed Oct. 11, 2000 now abandonded. This application is a regular U.S. patent application under 35 U.S.C. §111(a) and 35 U.S.C. §1.53(b) and claims priority from the following co-pending, commonly assigned provisional application filed under 35 U.S.C. §111(b): No. 60/194,652 filed Apr. 4, 2000.

FIELD OF THE INVENTION

The present invention relates to a chromatographic method for detecting heteroduplexes in nucleic acid fragments, and particularly to denaturing anion-exchange high performance liquid chromatography, for use in detecting mutations.

BACKGROUND OF THE INVENTION

The ability to detect mutations in double stranded polynucleotides, and especially in DNA fragments, is of great importance in medicine, as well as in the physical and social sciences. The Human Genome Project is providing an enormous amount of genetic information which is setting new criteria for evaluating the links between mutations and human disorders (Guyer et al., *Proc. Natl. Acad. Sci. USA* 92:10841 (1995)). The ultimate source of disease, for example, is described by genetic code that differs from wild type (Cotton, *TIG* 13:43 (1997)). Understanding the genetic basis of disease can be the starting point for a cure. Similarly, determination of differences in genetic code can provide powerful and perhaps definitive insights into the study of evolution and populations (Cooper, et. al., *Human Genetics* 69:201 (1985)). Understanding these and other issues related to genetic coding is based on the ability to identify anomalies, i.e., mutations, in a DNA fragment relative to the wild type. A need exists, therefore, for a methodology to detect mutations in an accurate, reproducible and reliable manner.

DNA molecules are polymers comprising sub-units called deoxynucleotides. The four deoxynucleotides found in DNA comprise a common cyclic sugar, deoxyribose, which is covalently bonded to any of the four bases, adenine (a purine), guanine(a purine), cytosine (a pyrimidine), and thymine (a pyrimidine), hereinbelow referred to as A, G, C, and T respectively. A phosphate group links a 3'-hydroxyl of one deoxynucleotide with the 5'-hydroxyl of another deoxynucleotide to form a polymeric chain. In double stranded DNA, two strands are held together in a helical structure by hydrogen bonds between, what are called, complementary bases. The complimentarity of bases is determined by their chemical structures. In double stranded DNA, each A pairs with a T and each G pairs with a C, i.e., a purine pairs with a pyrimidine. Ideally, DNA is replicated in exact copies by DNA polymerases during cell division in the human body or in other living organisms. DNA strands can also be replicated in vitro by means of the Polymerase Chain Reaction (PCR).

Sometimes, exact replication fails and an incorrect base pairing occurs, which after further replication of the new strand results in double stranded DNA offspring containing a heritable difference in the base sequence from that of the parent. Such heritable changes in base pair sequence are called mutations.

In the present invention, double stranded DNA is referred to as a duplex. When the base sequence of one strand is entirely complementary to base sequence of the other strand, the duplex is called a homoduplex. When a duplex contains at least one base pair which is not complementary, the duplex is called a heteroduplex. A heteroduplex duplex is formed during DNA replication when an error is made by a DNA polymerase enzyme and a non-complementary base is added to a polynucleotide chain being replicated. Further replications of a heteroduplex will, ideally, produce homoduplexes which are heterozygous, i.e., these homoduplexes will have an altered sequence compared to the original parent DNA strand. When the parent DNA has the sequence which predominates in a natural population it is generally called the "wild type."

Many different types of DNA mutations are known. Examples of DNA mutations include, but are not limited to, "point mutation" or "single base pair mutations" wherein an incorrect base pairing occurs. The most common point mutations comprise "transitions" wherein one purine or pyrimidine base is replaced for another and "transversions" wherein a purine is substituted for a pyrimidine (and visa versa). Point mutations also comprise mutations wherein a base is added or deleted from a DNA chain. Such "insertions" or "deletions" are also known as "frameshift mutations". Although they occur with less frequency than point mutations, larger mutations affecting multiple base pairs can also occur and may be important. A more detailed discussion of mutations can be found in U.S. Pat. No. 5,459,039 to Modrich (1995), and U.S. Pat. No. 5,698,400 to Cotton (1997). These references and the references contained therein are incorporated in their entireties herein.

The sequence of base pairs in DNA codes for the production of proteins. In particular, a DNA sequence in the exon portion of a DNA chain codes for a corresponding amino acid sequence in a protein. Therefore, a mutation in a DNA sequence may result in an alteration in the amino acid sequence of a protein. Such an alteration in the amino acid sequence may be completely benign or may inactivate a protein or alter its function to be life threatening or fatal. On the other hand, mutations in an intron portion of a DNA chain would not be expected to have a biological effect since an intron section does not contain code for protein production. Nevertheless, mutation detection in an intron section may be important, for example, in a forensic investigation.

Detection of mutations is, therefore, of great interest and importance in diagnosing diseases, understanding the origins of disease and the development of potential treatments. Detection of mutations and identification of similarities or differences in DNA samples is also of critical importance in increasing the world food supply by developing diseases resistant and/or higher yielding crop strains, in forensic science, in the study of evolution and populations, and in scientific research in general (Guyer et al. (1995); Cotton (1997)). These references and the references contained therein are incorporated in their entireties herein.

Alterations in a DNA sequence which are benign or have no negative consequences are sometimes called "polymorphisms". In the present invention, any alterations in the DNA sequence, whether they have negative consequences or not, are called "mutations". It is to be understood that the method of this invention has the capability to detect mutations regardless of biological effect or lack thereof. For the sake of simplicity, the term "mutation" will be used throughout to mean an alteration in the base sequence of a DNA strand compared to a reference strand. It is to be understood that in the context of this invention, the term "mutation" includes the term "polymorphism" or any other similar or equivalent term of art.

There exists a need for an accurate and reproducible analytical method for mutation detection which is easy to implement. Such a method, which can be automated and provide high throughput sample screening with a minimum of operator attention, is also highly desirable.

Analysis of DNA samples has historically been done using gel electrophoresis. Capillary electrophoresis has been used to separate and analyze mixtures of DNA. However, these methods cannot distinguish point mutations from homoduplexes having the same base pair length.

The "heteroduplex site separation temperature" is defined herein to include the temperature at which one or more base pairs denature, i.e., separate, at the site of base pair mismatch in a heteroduplex DNA fragment. Since at least one base pair in a heteroduplex is not complementary, it takes less energy to separate the bases at that site compared to its fully complementary base pair analog in a homoduplex. Local denaturation of the heteroduplex creates what is generally called a "bubble" at the site of base pair mismatch. The bubble distorts the structure of a DNA fragment compared to a fully complementary homoduplex of the same base pair length. This structural distortion under partially denaturing conditions has been used in the past to separate heteroduplexes and homoduplexes by denaturing gel electrophoresis and denaturing capillary electrophoresis. However, these techniques are operationally difficult to implement and require highly skilled personnel. In addition, the analyses are lengthy and require a great deal of set up time. A denaturing capillary gel electrophoresis analysis of a 90 base pair fragment takes more than 30 minutes and a denaturing gel electrophoresis analysis may take 5 hours or more. The long analysis time of the gel methodology is further exacerbated by the fact that the movement of DNA fragments in a gel is inversely proportional to the length of the fragments.

In addition to the deficiencies of denaturing gel methods mentioned above, these techniques are not always reproducible or accurate since the preparation of a gel and running an analysis is highly variable from one operator to another.

Two major liquid chromatographic separation chemistries are used for DNA: anion exchange and ion-paired reverse-phase. In anion exchange, the solid chromatographic matrix contains on its surface abundant fixed positive charges which bind the DNA polyanion with a strength related directly to DNA length. As the concentration of an eluting salt is increased, usually continuously with elution time and the volume of mobile phase passed through a cylindrical column of the densely packed matrix, DNA fragments are eluted in approximate order of increasing size, because dissolved salt weakens the binding of polyanion to matrix. In U.S. Pat. Nos. 5,856,192 and 5,866,429, Bloch describes methods for salt-gradient anion-exchange separation of nucleic acids under non-denaturing conditions.

Recently, Ion Paired Reverse Phase HPLC (IPRPHPLC) was introduced to effectively separate mixtures of double stranded polynucleotides, in general and DNA, in particular, wherein the separations are based on base pair length (U.S. Pat. No. 5,585,236 to Bonn (1996); Huber, et al., *Chromatographia* 37:653 (1993); Huber, et al., *Anal. Biochem.* 212:351 (1993)).

As the use and understanding of IPRPHPLC developed it became apparent that when IPRPHPLC analyses were carried out at a partially denaturing temperature, i.e., a temperature sufficient to denature a heteroduplex at the site of base pair mismatch, homoduplexes could be separated from heteroduplexes having the same base pair length (Hayward-Lester, et al., *Genome Research* 5:494 (1995); Underhill, et al., *Proc. Natl. Acad. Sci. USA* 93:193 (1996); Doris, et al., *DHPLC Workshop,* Stanford University, (1997); U.S. Pat. No. 5,795,976). Thus, the use of DHPLC was applied to mutation detection (Underhill, et al., *Genome Research* 7:996 (1997); Liu, et al., *Nucleic Acid Res.,* 26;1396 (1998)).

SUMMARY OF THE INVENTION

Accordingly, one object of the present invention is to provide a method for detecting mutations in nucleic acids which is accurate, i.e., practically free of misleading results (e.g. "false positives"), is convenient to use, makes it possible to rapidly obtain results, is reliable in operation, is simple, convenient and inexpensive to operate.

Another object of the present invention is to provide a method for detecting mutations which utilizes an anion-exchange chromatographic method for separating polynucleotides with improved and predictable separation and efficiency.

Yet another object of the invention is to provide an improved method for selecting the temperature for conducting an anion-exchange chromatographic separation of nucleic acids for mutation detection.

Still yet another object of the invention is to provide a method which can be automated.

These and other objects which will become apparent from the following specification have been achieved by the present invention.

In one aspect, the present invention provides a method for separating heteroduplex and homoduplex nucleic acid molecules (e.g., DNA or RNA) in a mixture using anion-exchange chromatography and preferably anion-exchange high performance chromatography. In the separation method, a mixture containing both heteroduplex and homoduplex nucleic acid molecules is applied to a stationary anion-exchange support. The sample mixture is then eluted with a mobile phase containing an eluting salt, a buffer, and preferably an organic solvent. Sample elution is carried out under conditions effective to at least partially denature the heteroduplexes and results in the separation of the heteroduplex and homoduplex molecules.

Stationary phases for carrying out the separation include supports composed of silica, polysaccharide or synthetic polyolefin backbone. The polyolefin can be polystyrene or polyacrylic, for example. The stationary phase is preferably an anion exchange solid with an average diameter between approximately 2 micron and 10 micron.

In the present method, the mobile phase includes an eluting salt, an organic solvent, and a buffer. In one embodiment, the mobile phase pH is preferably in the range of 4 to 9, and contains an eluting salt composed of equal concentrations of: a cation selected from the group consisting of choline, sodium, potassium, lithium, guanidinium, dialkylammonium, trialkylammonium and tetraalkylammonium wherein the alkyl groups consist of any combination of methyl and ethyl; and an anion selected from the group consisting of bromide, chloride, acetate, formate, nitrate, perchlorate, dihydrogen phosphate, ethane sulfonate, and methane sulfonate; a buffer acid with a pKa in the approximate range of 3.5 to 9.5; and, an organic solvent; wherein the concentration of eluting salt is systematically increased from approximately 0.1 to approximately 5M, and preferably approximately 0.5M to approximately 2.0M.

Organic solvent that are water soluble are preferably used in the instant invention, for example, alcohols, nitriles, dimethylformamide (DMF), tetrahydrofuran (THF), esters, and ethers. Water soluble solvents are defined as those which exist as a single phase with aqueous systems under all conditions of operation of the present invention. Solvents which are particularly preferred for use in the method of this invention include methanol, ethanol, 2-propanol, 1-propanol, tetrahydrofuran (THF), formamide, N-methyl pyrrolidone, and acetonitrile, with acetonitrile being most preferred overall.

In one embodiment, the mobile phase for carrying out the separation of the present invention contains between about 5% to about 80% by volume, and preferably less than about 40% by volume, of an organic solvent; about 0.5M to about 2M eluting salt; and a buffer having a concentration of up to about 0.5M and preferably between 0.01M to about 0.1M, with a pH in the range of about 4 to about 10.

At least partial denaturation of heteroduplex molecules can be carried out several ways including the following. Column temperatures for carrying out the separation method of the invention are typically between about 30° C. and 90° C., and preferably between about 50° and about 80° C., most preferably between about 65° and 75° C. In a preferred embodiment, the separation is carried out at a column temperature of 73° C. Alternately, sample elution can be carried out under pH conditions effective to at least partially denature the heteroduplex molecules. In such cases, a lower column temperature less than about 73° C. may be sufficient for the separation of the heteroduplex and homoduplexes molecules in the sample.

In the separation method of the present invention, the pH of the mobile phase will vary depending upon the nature and concentrations of various components, and is typically maintained between about 7 and 9. In one preferred embodiment, the mobile phase is maintained at a pH of 8.0, to obtain improved sample resolution.

In one particular embodiment of the present method, homoduplex and heteroduplex molecules in a mixture are separated by applying the mixture to a diethylaminoethyl functionalized polyacrylate support and eluting the mixture with a mobile phase containing choline chloride, Tris-Cl (at a pH of 8.0) and 15% acetonitrile as the organic solvent at a column temperature between about 70°–77° C.

In a preferred embodiment, the homoduplex and heteroduplex molecules contained in the mixture are amplified using the polymerase chain reaction and the amplified DNA molecules are denatured and renatured to form a mixture of heteroduplex and homoduplex molecules prior to carrying out the separation method of the invention.

In another aspect, the invention provides a method for detecting DNA genetic mutations, the method includes: a) heating a mixture of a sample double stranded DNA segment and a corresponding wild type double stranded DNA segment to a temperature at which the strands are completely denatured; b) cooling the product of step (a) until the strands are completely annealed, whereby a mixture comprising two homoduplexes and two heteroduplexes is formed if the sample segment includes a mutation; c) determining the heteromutant site separation temperature; d) analyzing the product of step (b) with Denaturing Anion-Exchange High Performance Chromatography at the heteromutant site separation temperature to identify the presence of any heteromutant site separated components therein. The heteromutant site separation temperature can be determined by analyzing the product of step (b) by Denaturing Anion-Exchange High Performance Liquid Chromatography in a series of incremental Denaturing Anion-Exchange High Performance Liquid Chromatography separations in the mutation separation temperature range, each successive separation having a higher temperature than the preceding separation until a mutation separation profile is observed or the absence of any mutation separation profile in the mutation separation temperature range is observed, wherein a mutation separation profile identifies the presence of a mutation and the absence of a mutation separation profile indicates an absence of mutation in the sample. Alternatively, the heteromutant site separation temperature is determined by analyzing the product of step (b) by Denaturing Anion-Exchange High Performance Liquid Chromatography in a series of incremental Denaturing Anion-Exchange High Performance Liquid Chromatography separations in the mutation separation temperature range, each successive separation having a lower temperature than the preceding separation until a mutation separation profile is observed or the absence of any mutation separation profile in the mutation separation temperature range is observed, wherein a mutation separation profile identifies the presence of a mutation and the absence of a mutation separation profile indicates an absence of mutation in the sample.

In another aspect, the invention concerns a composition which includes the mobile phase (preferably containing an eluting salt, a buffer, and an organic solvent) with an anion-exchange solid.

These and other objects and features of the invention will become more fully apparent when the following detailed description is read in conjunction with the accompanying figures and examples.

DETAILED DESCRIPTION OF THE INVENTION

Figure 1:
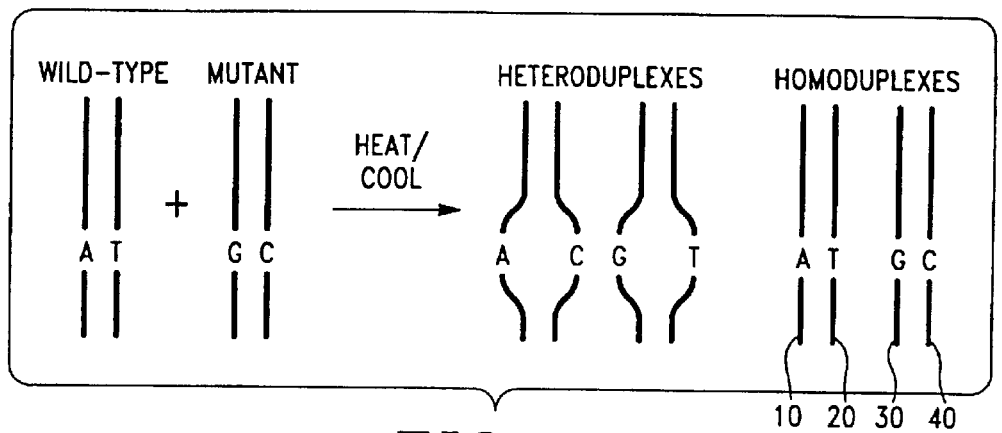
FIG. 1 shows a schematic representation of a hybridization to form homoduplex and heteroduplex molecules.

In one aspect, the present invention concerns a system and method for use in conducting DNA mutation detection. The instant invention can be used to detect mutations in double stranded DNA. The following definitions will be used herein:

A "homoduplex" is defined herein to include a double stranded DNA fragment wherein the bases in each strand are complementary relative to their counterpart bases in the other strand.

A "heteroduplex" is defined herein to include a double stranded DNA fragment wherein at least one base in each strand is not complementary to at least one counterpart base in the other strand. "Heteroduplex molecules" are typically composed of two complementary nucleic acid strands (e.g., DNA or RNA), where the strands have less than 100% sequence complementarity. This can be due to a mismatched base or a deletion. Since at least one base pair in a heteroduplex is not complementary, it takes less energy to separate the bases at that site compared to its fully complementary base pair analog in a homoduplex. This results in a bubble at the site of a mismatched base of a hetroduplex compared to a homoduplex.

The term "hybridization" includes a process of heating and cooling a dsDNA sample, e.g., heating to 95° C. followed by slow cooling. The heating process causes the DNA strands to denature. Upon cooling, the strands re-combine into duplexes in a largely statistical fashion. If the sample contains a mixture of wild type and mutant DNA, then hybridization will form a mixture of hetero- and homoduplexes.

The "heteromutant site separation temperature" T(hsst) includes the temperature which preferentially denatures the heteroduplex DNA at a site of mutation and which gives the greatest difference in the degree of denaturation between the heteroduplexes and homoduplexes. This is a temperature which is optimal to effect a chromatographic separation of heteroduplexes and homoduplexes by DAEHPLC and hence, detect mutations.

The term "heteromutant" includes a DNA fragment containing a polymorphism or non-complementary base pair.

The term "mutation separation profile" is defined herein to mean a DEAHPLC separation chromatogram which shows the separation of heteroduplexes from homoduplexes. Such separation profiles are characteristic of samples which contain mutations or polymorphisms and have been hybridized prior to being separated. The DEAHPLC separation chromatogram shown in FIG. 2 which was performed at 73° C. exemplifies a mutation separation profile as defined herein.

"Organic solvent" as used herein, includes a component of the mobile phase utilized in DAEHPLC. The organic solvent, occasionally referred to as an organic modifier, is any organic (e.g., non-aqueous) liquid suitable for use in the chromatographic separation methods of the present invention. Generally, the organic solvent is a polar solvent (e.g., more polar than the stationary support) such as acetonitrile or methanol.

"Base-pair mismatches" typically refers to a single base-pair mismatch flanked by matched base-pairs. Base-pair mismatches also include a series of mismatched base-pairs flanked by matched base-pairs. Base-pair mismatches can occur in heteroduplexes.

A heteroduplex molecule that is "at least partially denatured" under a given set of chromatographic conditions refers to a molecule in which several complementary base pairs of the duplex are not hydrogen-bond paired, such denaturing typically extending beyond the site of the base-pair mismatch contained in the heteroduplex, thereby enabling the heteroduplex to be distinguishable from a homoduplex molecule of essentially the same size. In accordance with the present invention, such denaturing conditions may be either chemically (e.g., resulting from pH conditions) or temperature-induced, or may be the result of both chemical and temperature factors.

A reliable way to detect mutations is by hybridization of the putative mutant strand in a sample with the wild type strand (Lerman, et al., *Meth. Enzymol.,* 155:482 (1987)). If a mutant strand is present, then two homoduplexes and two heteroduplexes will be formed as a result of the hybridization process, as shown in FIG. 1. Hence separation of heteroduplexes from homoduplexes provides a direct method of confirming the presence or absence of mutant DNA segments in a sample.

An embodiment of the present invention is a method for selection of the T(hsst) based on the temperature titration. In this embodiment, a sample containing the mutation is examined at a series of temperatures using a heuristic optimization approach. The optimum temperature obtained by this procedure is the temperature at which the mutant DNA fragment is most easily distinguished from the wild-type DNA by the difference in the pattern of peaks.

Nucleic acids comprise oligomers or polymers of pentose, connected by phosphoryl groups in phosphodiester linkage between the 5'-OH of one pentose and the 3'-OH of the next pentose, and each pentose carries an aromatic heterocyclic "base" in glycosidic linkage to the 1 carbon. If the pentose is ribose, the nucleic acid is RNA. If the pentose is 2-deoxyribose, the nucleic acid is DNA. Each phosphoryl group, except any at the end of a nucleic acid polymer, carries a single negative charge at pH values above about 2 to 3, so that the total negative charge of a nucleic acid is approximately proportional to its length, often expressed in units of nucleotides (nt) or base pairs (bp). Any of a wide variety of bases may be attached to the pentose, but only five predominate in naturally occurring DNA and RNA: adenine ("A"), thymine ("T", only in DNA), uracil ("U", primarily in RNA), guanine ("G"), and cytosine ("C") RNA usually consists of a single ribonucleotide polymer chain. Single stranded DNA is a single, deoxyribonucleotide polymer chain. However, two DNA chains of approximately complementary base sequence can dimerize to form double-stranded DNA. DNA and RNA chains of approximately complementary base sequence can dimerize to form a DNA-RNA hybrid similar in structure to double-stranded DNA.

Often an individual DNA or RNA chain has approximately mutually complementary base sequences in different parts of the polymer chain which permit folding to create locally double-stranded regions. Base complementarily follows simple rules: A can pair with T or U; G can pair with C; the most stable double-stranded structures occur when the two chains have "antiparallel" orientation, such that the 5'-OH end of one chain is base-complementary to the 3'-OH end of the other chain.

An anion-exchange separation is a process wherein fixed positive charges in one phase, usually solid but occasionally liquid, bind negative molecules in a second phase, usually liquid, contacting the first phase. The bound negative molecules can be separated from electrically neutral or positive molecules in the second phase simply by separation of the two phases. They can be separated from one another by contacting the first phase with fresh liquid of different composition from the original second phase such that the new composition weakens the attraction of more weakly bound anions to the first phase more than it does the attraction of more strongly bound anions to the first phase. Strength of anion attraction to the first phase varies directly with total negative charge of the anion. A bound anion is "eluted" when a new liquid succeeds in displacing it from the first phase. If the second phase is repeatedly replaced with liquids which progressively interfere more and more strongly with anion binding to the first phase, the process is called a "gradient elution." If the eluting liquid is changed in composition smoothly over time rather than in successive steps, the gradient elution is "continuous"; otherwise it is "stepwise" elution.

Preferably, the first phase is a solid. This "anion-exchange solid" consists of an electrically neutral "backbone" material which defines its size, shape, porosity, and mechanical properties, and positively charged "functional groups", preferably attached covalently to the backbone. The three most common classes of backbone materials are silica, polysaccharides, and synthetic polyolefins; the two major polyolefin subclasses are polystyrene and the polyacrylics. The latter comprise polymers of various substituted acrylic acid amides ("polyacrylamides") and acrylic acid esters ("polyacrylates"), wherein the acrylic monomer may or may not have alkyl substituents on the 2- or 3-carbon. The two most common positive functional groups are diethyl aminoethyl (DEAE; $[(CH_3CH_2)_2N-CH_2-CH_2-]_n$), attached covalently to the backbone, and polyethylene imine (PEI; $[-CH_2CH_2NH-]_n$), which may be covalently attached or noncovalently adsorbed to the backbone. When a liquid contacting the anion-exchange solid is an aqueous solvent of pH below about 9 to 11, the nitrogen atoms of DEAE and PEI are protonated and therefore positively charged. The lower the pH, the larger the fraction of functional groups that is cationic. The pH region over which most functional groups in a given anion-exchange solid are positively charged depends primarily on the backbone structure and the density of functional groups on the surface of the backbone. Other suitable anion exchange resins include positive functional groups such as quaternary amino groups. An example includes trimethyl amino methyl benzyl polymer.

Most commonly in anion-exchange separations, the eluting liquid is an aqueous electrolyte; and gradient elution is accomplished by increasing the concentration of a completely dissociated salt dissolved in the water. Increasing the eluting salt concentration in the anion-exchange solvent weakens the binding of anions, such as nucleic acids, to the anion-exchange solid. For purposes of the present invention, the eluting salt, which can be present in the approximate concentration range of about 0.1 to about 5M, and preferably in the range of about 0.5 to about 2M, consists of a di-, tri-, or tetraalkylammonium cation and any of a variety of mono-anions, preferably formate, acetate, chloride, bromide, nitrate, perchlorate, methanesulfonate, dihydrogen phosphate, or ethane sulfonate. Preferably, the alkyl groups on the ammonium cation are methyl or ethyl groups with methyl most preferred. Cations containing both methyl and ethyl groups also are allowed but are harder to prepare than cations containing only one or the other alkyl group. The eluting salt can be prepared as a solid which is dissolved in water to make the eluting solvent, or a solution of eluting salt can be prepared by mixing the acid constituting the protonated monoanion (e.g., formic, acetic, or hydrochloric acid) in equimolar stoichiometry with an aqueous solution of the alkylamine or alkylammonium hydroxide.

Other examples of suitable cations for use in the present invention include sodium, potassium, lithium, guanidinium and choline. These can be used in the concentration range of about 0.1 M to about 5M, and preferably in the range of about 0.5M to about 2M.

Mixtures of the cations described herein can also be used in the invention. Mixtures of the described anions can also be used.

In certain embodiments, the amino acid analogue betaine, in the range of about 0.5M to about 6M, can be used as the eluting salt in the mobile phase of the instant invention to elute double stranded DNA in the present invention. This has the advantage of lowering the base pair composition dependence of DNA melting (Rees et al. Biochemistry 32:137–144, 1993).

The anion-exchange solvents not only contain a dissolved alkylammonium salt but also are buffered at a pH between about 2 and about 11, and preferably between about 4 and about 9, by adding a weak acid with a pKa (the pH at which half of the acid molecules have lost a proton) between about 2 and about 11, and preferably between about 3.5 and about 9.5, together with enough base to achieve the desired pH. Preferably, the buffer acid concentration will not exceed about 0.5M and more preferably will be less than about 0.5M. Also preferably, the buffer acid is itself cationic (i.e., it may be supplied as the salt of the buffer acid cation and the anionic conjugate base of another acid, usually a strong mineral acid), so that its conjugate base is not anionic. An anionic buffer conjugate base might bind to the anion-exchange solid in a way which lowers the pH from the desired value. Particularly preferred buffer acids are provided by the "zwitterionic buffers", originally described by Good et al., 1966, Biochemistry 5:467–477, and now commonly available at high purity from biochemical reagent companies. Non-limiting examples of suitable buffers include: BES, BICINE, CAPS, EPPS, HEPES, MES25, MOPS, PIPES, TAPS, TES, and TRICINE A preferred anion-exchange separation process is "chromatography", wherein the anion-exchange solid, usually in particulate form, is contacted with continuously flowing anion-exchange solvent, which efficiently carries nucleic acids to the solid for the initial binding reaction and efficiently removes them from the solid as the eluting salt concentration is increased. Particulate anion-exchange solid preferably is packed in a cylindrical column; solvent flows in one end of the column and out the other. An especially preferred mode of liquid chromatography is HPLC, wherein the anion-exchange solid particles are so small (normally 2–10 $\mu$m in diameter) and are packed so tightly that high pressures (hundreds to several thousand pounds per square inch) are needed to force solvent through the column. Such small particles undergo anion-exchange binding and elution reactions very rapidly, permitting separations on the time scale of a few minutes, which still allow the separation from one another of many different nucleic acid species of lengths ranging over one to two orders of magnitude (e.g., 50 to 500 or 5,000 base pairs).

In one aspect, the present invention provides a method for separating heteroduplex and homoduplex DNA molecules in a mixture using anion-exchange high performance liquid chromatography and more particularly, denaturing anion-exchange high performance liquid chromatography, as will be described in detail below. The method can be utilized for detecting a single base mismatch in a DNA duplex containing up to about 2000 base pairs.

High performance liquid chromatography (HPLC) generally refers to a technique for partitioning a sample or more specifically the components of a sample between a liquid moving or mobile phase and a solid stationary phase. In the present invention, the applicants have discovered a chromatographic method which utilizes conditions effective for at least partially denaturing heteroduplexes during sample elution to thereby enable the separation and identification of heteroduplexes and homoduplexes contained in a mixture.

A reliable way to detect mutations is by hybridization of the putative mutant strand in a sample with the wild type strand (Lerman, et al., Meth. Enzymol., 155:482 (1987)). If a mutant strand is present, then two homoduplexes and two heteroduplexes will be formed as a result of the hybridization process, as shown in FIG. 1. Hence separation of heteroduplexes from homoduplexes provides a direct method of confirming the presence or absence of mutant DNA segments in a sample.

In preferred embodiments if the instant invention, chromatographic resolution of heteroduplexes from homoduplexes is achieved by using gradient elution at a temperature which is just starting to denature the DNA at the site of mismatch. The heteroduplexes are destabilized by the mismatched bases and therefore are slightly more denatured than the homoduplexes at this temperature. Applicants have made the novel and unexpected observation that in DAEHPLC, the retention time of the heteroduplexes differs from the homoduplexes. Without wishing to be bound by theory, it is believed that the partial denaturation of the heteroduplexes causes them to have a different affinity for the separation medium than the homoduplexes, and therefore to elute at a different time (at a longer retention time) than the relatively undenatured homoduplexes.

In the method of the present invention, a sample mixture containing both heteroduplex and homoduplex molecules is applied to a stationary phase. Generally, the stationary phase is an anion-exchange support as described hereinbelow. Any of a number of commercially available anion-exchange reverse phase solid supports may be utilized in the present nucleic acid separation method although the resolution and the order of the peaks may vary depending upon the nature of the sample and other relevant experimental parameters.

A stationary phase for use in the present method typically has pores with sizes ranging from less than about 30 Å in diameter (e.g., nonporous materials) up to about 1000 Å in size. In using nonporous polymeric support materials, the relatively small pore size excludes many sample compounds from permeating the pore structure and may promote increased interaction with the active surface. The stationary phase may also contain more than one type of pore or pore system, e.g., containing both micropores (less than about 50 Å) and macropores (greater than about 1000 Å).

For achieving separations of samples containing heteroduplexes and homoduplexes of up to about 2000 base pairs in size, the stationary phase will typically have a surface area of about 2–400 m2/g, and preferably about 8–20 m2/g as determined by nitrogen adsorption.

In a preferred embodiment, the separation method of the present invention utilizes DAEHPLC. In carrying out the separation according to the present method, the aqueous mobile phase contains an eluting salt, a buffer, and preferably an organic solvent.

The selection of aqueous mobile phase components will vary depending upon the nature of the sample and the degree of separation desired. Any of a number of mobile phase components typically utilized in anion-exchange HPLC are suitable for use in the present invention. Several mobile phase parameters (e.g., pH, organic solvent, salt, buffer, elution gradient) may be varied to achieve optimal separation.

Salts for use in the invention are those which contain an anion which interacts with the cationic groups on the surface of the separation support.

The pH of the mobile phase will vary depending upon the concentrations of various components. For separation of nucleic acid samples such as RNA or DNA fragments, using temperature to effect at least partial denaturation of the nucleic acid, the pH of the mobile phase is typically maintained between about 7 and 9. Preferably, the mobile phase is maintained at a pH around 7.5.

In an alternate embodiment, the pH of the mobile phase is adjusted to effect at least partial denaturation of the heteroduplex molecules in a sample containing a mixture of homoduplexes and heteroduplexes to allow separation and detection of the heteroduplex molecules. In using chemical means to effect heteroduplex denaturation, the pH may be adjusted by addition of either base (e.g., sodium hydroxide or urea to a pH of around about 8) or acid (e.g., triethylamine and acetic acid at a pH of about 8) under conditions effective to at least partially denature the heteroduplex molecules and which do not degrade the nucleic acids present in the sample nor adversely affect the integrity of the stationary phase. In such cases, sample elution may be carried out at temperatures less than about 60° C.

The concentration of the mobile phase components will vary depending upon the nature of the separation to be carried out. The mobile phase composition may vary from sample and during the course of the sample elution. Gradient systems containing two or more components may be used. The present invention is based in part on the surprising observation by Applicants that the presence of organic solvent in the mobile phase lowers the T(hsst) to a more manageable value during DAEHPLC. In general, the T(hsst) decreases as the percent of organic solvent in the mobile phase increases.

Samples are typically eluted by starting with an aqueous or mostly aqueous mobile phase containing an eluting salt, a buffer, and preferably an organic solvent, and progressing to a mobile phase containing increasing amounts of an eluting salt. Any of a number of gradient profiles and system components may be used to achieve the denaturing conditions of the present invention. One such exemplary gradient system in accordance with the invention is a linear binary gradient system composed of (i) 0.02M Tris-Cl, pH=8.0, in 15% acetonitrile and (ii) 2M choline, 0.02M Tris-Cl pH=8.0, in 15% acetonitrile.

In other embodiments, the concentration organic solvent in the mobile phase can be varied in a gradient.

One way to achieve the denaturing conditions of the present invention (e.g., effective to at least partially denature heteroduplexes) is to modulate column temperature, as will be discussed in reference to the Examples below.

During the elution, the column temperature can be between about 30° C. and 90° C., preferably between 50° C. and 80° C. and more preferably between 65° C. and 85° C. The column temperature typically between about 65° and about 80° C. is preferred for resolving heteroduplex molecules from their corresponding homoduplex molecules by DAEHPLC chromatography. The optimal column temperature will depend upon the sequence (base composition) of the sample to be separated, the choice of stationary phase, the choice of mobile phase, pH, flow rate, and the like, and in many cases, will be determined empirically. Ideally, in cases with known sequence, a suitable column temperature may be calculated.

One aspect of the invention is a method which includes the steps of performing a temperature titration which includes analyzing the DNA mixture by DAEHPLC in a series of DAEHPLC separations in the temperature range of about 50° C. to about 80° C., each successive separation having a higher temperature than the preceding separation until a mutation separation profile is observed or the absence of any mutation separation profile in the mutation separation temperature range is observed, wherein a mutation separation profile identifies the presence of a mutation and the absence of a mutation separation profile indicates an absence of mutation in the sample. Alternatively, analyzing the mixture by DAEHPLC in a series of DAEHPLC separations in the temperature range of 50° C. to about 80° C., each successive separation having a lower temperature than the preceding separation until a mutation separation profile is observed or the absence of any mutation separation profile in the mutation separation temperature range is observed, wherein a mutation separation profile identifies the presence of a mutation and the absence of a mutation separation profile indicates an absence of mutation in the sample.

As will be seen from the discussion of the Examples below, heteroduplex detection can, in many cases, be accomplished at a column temperature of about 73° C.

In support of the method of the present invention, experiments have been carried out in which single base mismatches in heteroduplexes 209 base pairs in size have been detected, as will be described below.

In an exemplary method for detecting polymorphisms in nucleic acid fragments, experiments were carried out in which two different homoduplex molecules, identical in sequence with the exception of one base pair, were denatured and reannealed to form a mixture containing four resulting duplex products, two homoduplexes and two heteroduplexes. Details of the experiments are described in the Examples hereinbelow. A generalized scheme illustrating the mixture of products formed by denaturing and reannealing two such homoduplexes is provided in FIG. 1.

The exemplary polynucleotides used in the set of experiments described below were generally prepared as follows and as described in Example 2. The desired polynucleotide fragments were derived by cloning the representative allelic states of the human Y chromosome STS, sY81 (locus DYS271). STS sY81 displays a single point mutation, an A to G transition, at nucleotide position 168 within the 209 bp sequence tagged site (STS) (Seielstad, et al. *Human Molecular Genetics* 3:2159 (1994)). Initially, both the 209 bp "wild type" A allele and the African G allele forms were amplified from commercially obtained plasmids.

Briefly, as described in Example 2 for experiments performed with 209-mer duplexes, two double stranded polynucleotide PCR products, homo-A-209 and homo-G-209 were subjected to denaturation and reannealing.

Alternatively, a mixture containing the wild type and the G allele form of the 209 base pair fragment (Seielstad et al.) can be obtained commercially (e.g., part no. 440582, Transgenomic, Inc.) and subjected to denaturation and reannealing.

Double-stranded DNA homoduplex A, "homo-A-209", a 209-base pair fragment, was composed of two complementary 209-base fragments, polynucleotides 10 and 20 (FIG. 1). Double stranded DNA homoduplex G, "homo-G-209", a second 209-base pair fragment, was identical in sequence to homo-A-209 with the exception of one base pair (a G-C substituted for A-T present in homo-A-209) and was composed of polynucleotides 30 and 40. Polynucleotide 30 was identical in sequence to polynucleotide 10, with the exception of a guanosine at position 168 from the 5' end of polynucleotide 30, in comparison to an adenosine at the analogous position in polynucleotide 10. In a similar fashion, polynucleotide 40 was identical in sequence to polynucleotide 20, with the exception of a cytosine at position 42 from the 5' end replacing a thymidine in the same position in polynucleotide 20.

The resulting mixture of products, containing original homoduplexes homo-A-209 and homo-G-209 and newly formed heteroduplexes hetero-AC-209 and hetero-GT-209 were then analyzed under the denaturing conditions of the present invention using DAEHPLC. The designation hetero-AC-209 represents the double stranded product formed by annealing polynucleotides 10 and 40, and contains a single base pair A-C mismatch at position 168 relative to homo-A-209. The designation hetero-GT-209 represents the double stranded product formed by annealing polynucleotides 20 and 30, and contains a single base pair G-T mismatch at position 168 relative to homo-G-209.

Six separate runs were performed from 72° C. to 77° C. (FIG. 2) to optimize the effect of column temperature on separation of the product mixture components. As will be appreciated, using a given stationary support, adjustments in run parameters such as the components of the mobile phase and relative amounts thereof, pH, gradient profile, flow rate, column temperature, and the like, may be useful in selecting the optimal denaturing conditions for carrying out the separation method of the present invention.

Figure 2:
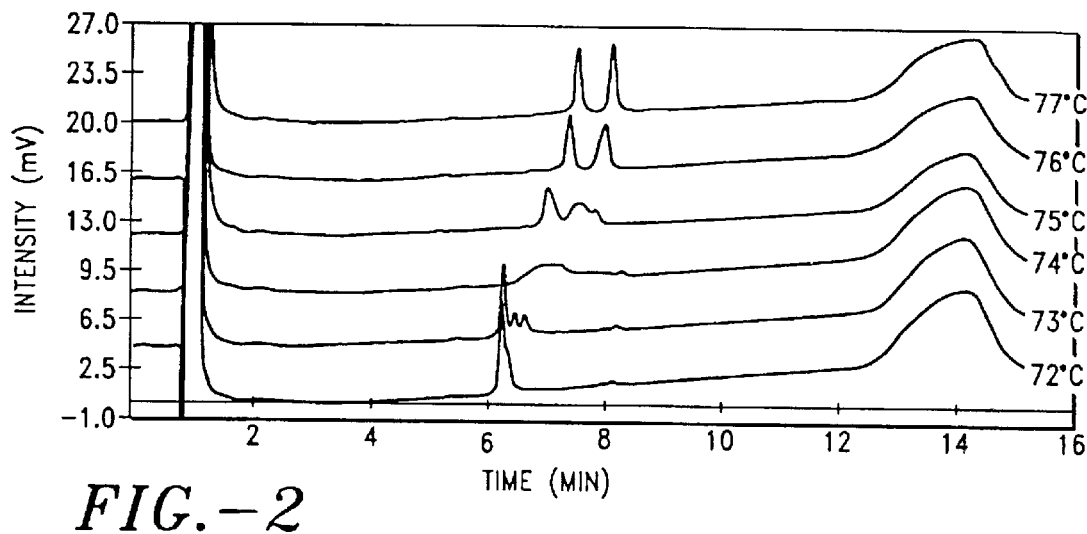
FIG. 2 shows a series of chromatograms resulting from denaturing anion-exchange HPLC on a diethylaminoethyl functionalized polyacrylate support and eluting separate injections of a mixture of 209 bp homoduplex and heteroduplex DNA molecules at a series of temperatures between about 72°–77° C.
Figure 3:
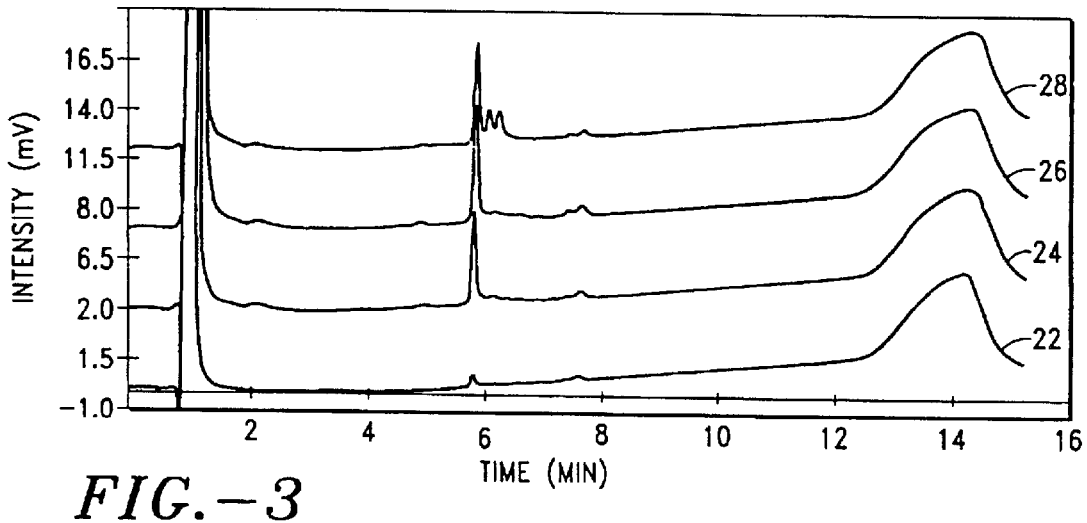
FIG. 3 shows a series of chromatograms resulting from denaturing anion-exchange HPLC on a diethylaminoethyl functionalized polyacrylate support and eluting separate injections of various 209 bp DNA preparations at a column temperature of 73° C.

At a less stringent column temperature of 72° C., separation/detection of the individual components of the product mixture containing homo-A-209, homo-G-209, hetero AC-209, and hetero-GT-209 was not achieved (FIG. 2). The components of the mixture co-eluted as a single peak, with a retention time about equivalent to that of each of homoduplexes homo-A-209 and homo-G-209 (FIG. 3). In FIG. 3, profiles 22,24,26, and 28 correspond to the A allele, the G allele, a mixture of unhybridized A and G alleles, and a mixture resulting from hybridization of the A and G alleles, respectively.

Upon raising the column temperature to 73° C., the resolution of the separation was significantly enhanced as is shown in FIG. 2. The homoduplex products were clearly separated from the heteroduplexes, which eluted from the column slightly later than did the homoduplexes.

The DNA fragments appear to be only partially denatured using the optimized denaturing chromatographic conditions of the present invention, resulting in the formation of a "bubble" at the site of the base-pair mismatch. The distortion of the DNA duplex caused by this partial denaturation or bubble appears to cause a shift towards longer retention times and allows the separation of heteroduplexes containing a single base pair mismatch from homoduplexes of the same size, as illustrated in FIG. 1.

The results described above show the effective separation of nucleic acid duplexes containing a single base pair mismatch from homoduplexes of the same size by partial denaturation of the heteroduplexes using the denaturing anion-exchange HPLC conditions described herein, leading to longer retention times.

The mutation separation profile preferably will show a distinct peak for each of the homoduplex and heteroduplex molecules. However, these peaks need not be fully separated in order to detect whether a mixture of homoduplex and heteroduplex is present. Thus the presence of a shoulder on a homoduplex peak, or partial separation of the peaks, can still provide useful information in detecting the presence of a mutaiton.

In carrying out the separation method of the present invention, a variety of factors may influence product resolution. While it is not possible to determine an ideal set of conditions suitable for analyzing all possible nucleic acid fragments by the present DAEHPLC method, based upon experiments performed to date, conditions determined to be preferred or found to affect sample resolution are discussed below.

In carrying out the DAEHPLC method of the invention, the nucleic acid sample to be analyzed is typically injected and pre-mixed with the mobile phase prior to elution on the solid support. The sample is then contacted directly with the stationary phase, or alternatively, is passed through a "pre-conditioning" tubing or pre-column to allow the sample and mobile phase to equilibrate before contact with the solid support.

In one embodiment, the mobile phase components are introduced into a mixer inside the column oven and mixed prior to contact with the sample. Alternatively, the mobile phase components may be mixed at ambient temperature and contacted with the sample injector, also maintained at ambient temperature outside of the column oven. Both of the above variations have been shown to be suitable for detection of heteroduplexes as has been described.

In a preferred embodiment, the sample is injected into the mobile phase, pre-equilibrated to the temperature of the column. In this manner, a near-direct connection between the column and the injector is provided to minimize diffusion and enhance sample resolution.

Alternately, when utilizing a low-pressure HPLC system, sample mixing typically occurs at ambient temperature. In instances in which the autosampler does not provide for heating the injection port to column temperature, standard HPLC tubing (e.g., 0.005–0.01 diameter) may be positioned between the injector and the column, to heat the mobile phase and induce partial denaturation of the DNA sample. The tubing is preferably fitted with non-DNA binding hardware such as that made of PEEK (polyether ether ketone) or titanium. The length of the tubing is typically determined based upon the efficiency of heat transfer. The entire length of the pre-column may be maintained at oven temperature, or, only a portion of the pre-column may be heated. The sample is passed through the pre-column and then contacted with the stationary phase for subsequent elution.

As has been discussed above, one parameter which impacts the DAEHPLC method of the present invention is pH. Generally, the pH of the mobile phase is maintained between about 2 and about 11, preferably between about 4 and about 9, and more preferably between about 7 and about 9. In attempting to observe a single base mismatch in a polynucleotide 209 base pairs in length, a preferred pH for carrying out the separation was found to be 8.0.

Another factor which affects the parameters to be selected for carrying out the separation method of the invention is the composition of the sample sequence to be analyzed. In this respect, for samples containing a polymorphic site flanked by a GC-rich region, higher temperatures may be required to detect the polymorphism.

The present invention provides a general method for screening for polymorphisms and sequence variations between similar nucleic acids isolated from different sources.

The DAEHPLC method of the present invention has potential applications in a wide variety of areas, including linkage analysis, evolutionary studies, forensics, identification of disease-causing gene mutations, genetic marker development, and the like. The method of the present invention requires only small amounts (typically less than about 100 nanograms) of unpurified sample, yields results in minutes, utilizes on-line detection, and is adaptable to complete automation.

The heteroduplex separation and detection method of the present invention based on heteroduplex formation (e.g., of PCR products) is faster, simpler, more sensitive and more informative than the currently available procedures (such as RNase A cleavage mismatch). The DAEHPLC method of the invention detects heteroduplex molecules in a mixture containing both heteroduplexes and homoduplexes by utilizing conditions effective to at least partially denature the heteroduplexes. Under such denaturing conditions, heteroduplexes exhibit slightly different retention times (typically longer) from their homoduplex counterparts, thus providing a sensitive and convenient assay for detecting heteroduplex formation.

Using the conditions described above, base pair mismatches and indels can be observed in heteroduplexes using the method of the present invention. The preferred size range for these heteroduplexes ranges from approximately 30 to 1000 base pairs in length, although larger-sized heteroduplexes can be used as well. In addition, more complex mixtures of restriction fragments (e.g., 100–1000 bp size range) resulting from the post-PCR digestion of longer amplification products can be surveyed for the presence of heteroduplexes.

In instances in which only homoduplexes are observed during the sample screening, further standard sequencing is not required since the sequence is monomorphic (i.e., lacking a polymorphic site) in all subjects compared. Alternatively, if an individual is homozygous for the mutation, then only homoduplexes would be observed during the sample screening. In utilizing the method of the present invention, only those DNA fragments identified as heteroduplexes, and therefore identified as containing at least one polymorphic site, are then sequenced by conventional methods to characterize the observed polymorphism(s).

Using the present DAEHPLC method, large numbers of comparative DNA samples can be rapidly and efficiently pre-screened for the presence (or absence) of polymorphisms, and only those samples identified in the pre-screening as possessing polymorphic sites need be further characterized, typically by conventional sequencing techniques. Such genomic analysis can be performed using any genomic nucleic acid material, for example, from mammals, fish, reptiles, plants, or other organisms of interest.

The present method can also be used for forensic applications such as DNA fingerprinting. DNA fingerprinting requires the identification of a set of polymorphic loci, selected so that the probability that two individual DNA samples with identical haplotypes could by chance come from different individuals is very low. The method provides an efficient approach for identifying low mutating polymorphic sites along lengths of contiguous sequence such that the probability of recombination is quite low, increasing the likelihood of the preservation of haplotype information desirable for forensic utilization.

In addition to analysis of genome diversity, the method of the present invention can be applied to the analysis of any number of microorganisms including bacteria, parasites, and other infectious agents. Exemplary microorganisms include, but are not limited to, the following:

(i) Bacterial. Haemophilus—outer membrane proteins, Staphylococcus, Chlamydia—outer membrane proteins, Enterococcus, Mycobacterium (Mycobacterium tuberculosis);

(ii) Viral. Feline Leukemia Virus (FeLV), Simian Immunodeficiency Virus (SIV), Human Immunodeficiency Virus (HIV), Hepatitis C Virus (HCV); Human papilloma virus (HPV);

(iii) Fungi. Pneumococcus—Choline dependent Pneumococcal murein hydrolases; 18S rDNA sequences for human pathogenic fungi including Trichophyton, Histoplasma, blastomyces, coccidioides, Pneumocystis (*Pneumocystis carinii*) and Candida (*Candida albicans*) (Bowman, et al. *Mol. Biol. and Evolution* 9:893–904 (1992));

(iv) Parasites. Onchocerca (Zimmerman, et al. *Mol. & Bio. Parasitology* 58:259–267 (1993)), Babesia spp. (Ellis, et al. *Mol. and Bio. Parasitology* 54:87–95

(1992)), Giardia spp. (Weiss, et al. *Mol. and Bio. Parasitology* 54:87–95 (1992)), Leishmania spp. (Briones, et al. *Mol. and Bio. Parasitology* 53:121–7 (1991)), Trypanosoma spp. (Breniere, et al. *Am. J. Trop. Med. and Hygiene* 46:335–1 (1992)); and (v) Mycoplasma. Lyme disease, Mycoplasma pneumoniae (Kleemola, et al. *Pediatric Infect Dis. J.* 12:344–5 (1993)), using, for example, sequences derived from 16S RNA.

Typically, probes for any target nucleic acid can be selected from a region of the microorganism's genomic material, such as rRNA (for example, as in Weisburg, et al. *J. Bacteriology* 171(12):6455–6467 (1989)). In this way probes can be identified that will form homoduplexes to identify specific species. Formation of heteroduplexes indicates that the sequences have diverged from the probe sequence.

The method of the present invention can also be applied to the analysis of any nucleic acid containing entity, including subcellular organelles such as chloroplasts and mitochondria.

Further, the method of the present invention can also be used in screening methods for the evaluation of therapeutic treatments of any of the above microorganisms. The methods disclosed herein are useful for evaluating, in mixtures of nucleic acids (such as, nucleic acids obtained from tissue samples), the effect over time of a disease treatment, on DNA sequence variation of a nucleic acid target sequence associated with the disease. Therapeutic treatments typically are directed to the resolution, elimination, or relief of a disease state, as, for example, caused by a microorganism/infectious agent.

In one exemplary application, the present method is used to monitor infection and any changes that might occur during treatment. As applied to infection, the DAEHPLC method of the invention can be used to establish a base-line of infection in any selected patient before the onset of treatment. Typically, blood and plasma samples are then serially collected from the subject throughout the therapeutic trial.

In one exemplary application, the method of the present invention can be used to monitor the effects of a disease treatment, such as in the case of tuberculosis (TB). The DAEHPLC separation method of the present invention can be used to monitor the presence and diversity of strains of Mycobacterium tuberculosis growing within an individual. For example, a 383 bp segment of the gene encoding the 65 kDa mycobacterial surface antigen can be amplified (Ghossein, et al. *Diagnostic Mol. Pathol.* 1(3):185–191 (1992)) from samples obtained from a patient under treatment and analyzed by the method of the present invention.

The present method can also be used to detect the specific loss or increase in abundance of TB variants during therapy.

Generally, the method of the present invention can be used to monitor when variants come and go within the course of any infection and what the impact of any treatment has on the variant populations. Specific loci associated with drug resistance for a particular microorganisms can be used for tracking different populations of a microorganism using the methods of the present invention, where the variant loci are amenable to detection using anion-exchange HPLC.

The present assay can be used to evaluate diversity in cell culture systems and animal models as well as patients.

Additionally, phylogenetic relationships can be established by the method of the present invention. Phylogenetic analysis can be carried out with almost any selected genomic sequence, such as, glycolytic enzymes (like phosphoglycerate kinase (Vohra, et al. *J. Mol. Eval.* 34:303–395 (1992))) or rRNA sequences. Phylogenic relationships between plants can be established, using, for example, sequences derived from plastid ribosomal RNA operons (Wolfe, et al. *Plant Molec. Biol.* 18(6):1037–1048 (1992)).

Another embodiment of the present invention is the use of specific probes to identify variants based on the formation of homoduplex complexes. For example, sequences corresponding to a particular virus variant can be cloned and amplified. These cloned sequences are then used as a probe against viral molecules isolated from a number of test sources. Using the method of the present invention, if homoduplexes are formed in hybridization reactions between the probe and the test source, then the test source is shown to be similar to the cloned probe variant. If on the other hand heteroduplexes are formed between the probe and test sequences, then sequence divergence between the probe and test sequences is indicated.

With respect to cancer, once a diagnosis has been made, and a region of DNA associated with the cancerous growth has been identified, the heteroduplex separation method of the present invention can be used to evaluate the extent of infiltration of tumor cells within a tissue population. Exemplary potential target sequences are protooncogenes, for example, including but not limited to the following: c-myc, c-myb, c-fos, c-kit, ras, BCR/ABL (e.g., Gazdar, et al. U.S. Pat. No. 4,892,829; Wickstrom (Wickstrom, E., Editor, PROSPECTS FOR ANTISENSE NUCLEIC ACID THERAPY OF CANCER AND AIDS, Wiley-Liss, New York, N.Y. (1991)); Zalewski, et al. *Circulation Res.* 88:1190–1195 (1993); Calabretta, et al., *Seminars in Cancer Biol.* 3(6):391–398 (1992); Calabretta, et al., *Cancer Treatment Rev.* 19(2):169–179 (1993)), and oncogenes/tumor suppressor genes (e.g., p53, Bayever, et al. *Antisense Research and Development* 3:383–390 (1993)). In tumor cells, deletions, insertions, rearrangements and divergent sequences in such genes or in the regions of DNA surrounding the coding sequences of such genes, all allow formation of heteroduplexes between amplified variant DNA and amplified DNA from normal cells.

In view of the above discussed applications, it can be seen that the method of the present invention provides the means to determine approximate levels of DNA sequence diversity in a population of nucleic acid sequences both within and between individuals.

Typically, samples to be analyzed by the method of the present invention are obtained by polymerase chain reaction amplification—the amplified sequences are denatured and reannealed before DAEHPLC analysis. In addition to obtaining nucleic acid samples by amplification, other samples sources can be used as well. For example, sequences of interest can be cloned (e.g., in a lambda vector; Sambrook, et al., in MOLECULAR CLONING: A LABORATORY MANUAL, Cold Spring Harbor Laboratory Press, Vol. 2 (1989)) from two different sources. The sequences of interest are independently isolated away from vector sequences (e.g., by restriction endonuclease digestion and fragment purification). These two samples can then be combined, denatured, renatured, and the resulting heteroduplexes analyzed in accordance with the present method.

A preferred way to provide the double stranded DNA for chromatographic analysis is the commonly known and practiced polymerase chain reaction (PCR), a method of greatly amplifying the number of molecules of one or a few specific nucleic acid sequences, most commonly in the size range of 50 to 1,000 bp, which is perfectly suited for anion-exchange HPLC separation on the basis of size. The PCR process is described in greater detail in U.S. Pat. Nos. 4,683,195; 4,683,202; 4,800,159; 4,889,818; and 4,965,188, each of which is incorporated herein by reference. Any single PCR tends to generate just one or a few DNA fragments in exactly the concentration range needed for UV absorbance detection of chromatographic peaks, between about $10^{-10}$M and $10^{-7}$M, especially if performed by a Hot Start™ method which uses the wax vapor barrier (described in U.S. patent application Ser. No. 481,501, filed Feb. 16, 1990, and incorporated herein by reference and as described by D'Aquila et al. *Nucleic Acids Res.* 19:3749 (1991)).

For purposes of the present invention, the test sample nucleic acid applied to the anion-exchange solid does not have to be significantly purified, so long as the test sample does not contain substantial amounts of UV-absorbing substances which bind as tightly as nucleic acids to the anion-exchange solid or which are eluted from the anion-exchange solid in the same salt concentration range effective for eluting the nucleic acids of interest. If such interfering substances are present, they commonly are removed by phenol-chloroform extraction and ethanol precipitation, as described in any commonly available manual of molecular biological techniques. Preferably the sample applied to the anion-exchange solid will have been treated to remove particulate material which might coat or clog the anion-exchange solid. Preferred modes of removing particulates include syringe-driven and centrifuge-driven passage through filters with pore sizes not larger than about 0.45 µm and simple centrifugation for at least 5 minutes of at minimally 10,000 rpm, for example, in a microcentrifuge. Filtration is preferred to centrifugation alone; both processes can be done with any of an abundance of commercially available equipment and disposable devices well known to the chemist, biologist, and molecular biologist. A final detail of test sample preparation is that preferably the nucleic acid should be dissolved in solvent approximating in composition the starting solvent of the gradient elution.

When the chromatographic analyte is double-stranded DNA but the test sample is expected to contain RNA or single-stranded DNA, two preferred modes exist to minimize the potential interference of the latter two types of nucleic acids with the elution profile of the analyte. One mode consists of first treating the test sample with a nuclease specific for RNA (for example, RNase A or RNase TI) or specific for single stranded DNA (for example, nuclease S1 from Aspergillus orvzae or mung bean nuclease) under enzyme concentration, temperature, and buffer composition conditions well known in the molecular biological art to protect double-stranded DNA from digestion by the same enzymes.

The other mode consists of first contacting the test sample with a solid material which binds single-stranded DNA under solvent and temperature conditions which strengthen this binding specificity. When the solid material to which the RNA or single stranded DNA has bound is then removed from the remaining liquid test sample (for example, by centrifugation or filtration), the latter is ready for application to the anion-exchange solid. Preferably this contacting is done in a solvent of approximately the same composition as the first solvent used in the chromatographic elution (for example, one containing a dialkylammonium, trialkylammonium, or tetraalkylammonium salt in the approximate concentration range of 0.5–1.0M).

Preferred solids for the specific binding of RNA and single-stranded DNA are nitrocellulose, most commonly available in membrane form, and any of a range of aralkylamines covalently attached to a solid support. Examples of such aralkylamines are phenylethylamine, phenylpropylamine, phenylbutylamine, and naphthyethylenediamine. A particularly convenient solid support is a particulate, epoxide-derivatized, porous or nonporous acrylic matrix, such as HEMA-1000 EH Bio, supplied by Alltech Associates, Inc. The aralkylamine can be reacted with the epoxide-bearing support following instructions supplied by Alltech. A commercially available immobilized aralkylamine is phenylbutylamine Eupergit (Rohm Pharma). However, it has inferior capacity, binding kinetics, and durability as compared to aralkylamine-modified epoxide-bearing HEMA. The amount of solid support used for test sample treatment can be minimized after trial-and-error testing of representative test samples, to simplify the recovery of treated sample from the solid.

One class of test sample wherein the HPLC analyte is double-stranded DNA, wherein interfering RNA or single-stranded DNA is likely to be present, and wherein the treatments just described are likely to be beneficial, is PCR product. If the initial PCR target is contained in genomic DNA, the genomic DNA will be substantially single stranded by the end of PCR thermal cycling. Test samples for PCR amplification often contain RNA as well. PCR product also is accompanied by unreacted primers, which are single-stranded synthetic oligonucleotides.

The anion-exchange solvents of the present invention are preferably made in deionized or glass-distilled water by standard chemical methods. Some eluting salts, such as tetramethylammonium chloride, are commercially available as highly purified solids. However, many must be prepared by mixing equimolar amounts of commercially available bases, such as trimethylamine and tetramethylammonium hydroxide, and acids, such as formic, acetic, nitric, perchloric, methane sulfonic, and ethane sulfonic acids. Component acid and base molarity can be determined in advance by titration to an indicator or potentiometric endpoint with acid or base standardized by the conventional methods of analytical chemistry. Because many of the commercially available alkylammonium salts are hygroscopic and many of the acids and bases are supplied as concentrated aqueous solutions of somewhat variable concentration, precision in solvent preparation is promoted by careful measurement of the conductivity, density, or refractive index of solutions made from carefully titrated components. Then later solutions can be adjusted in concentration to match recorded values of these easily measured physical properties, avoiding the more laborious methods of acid-base titration.

The final concentration of eluting salt in the solvents of the present invention generally will lie between 0.5 and 2M. When the eluting salt anion is the conjugate base of a strong acid (for examples, bromide, chloride, nitrate, perchlorate, methanesulfonate, and ethanesulfonate), the eluting salt provides little effective buffer capacity in the 4–9 pH range. Therefore, an additional buffer acid with a pKa within 1 pH unit (preferably within ½ pH unit) of the desired pH is added to the solvent to attain a final concentration, preferably in the range of 0.01 to 0.05M. Particularly preferred buffer acids are the synthetic zwitteronic buffers first described by Good et al., *Biochemistry* 5:467–477 (1966), or cationic acid species (protonated amines) provided as salts of their conjugate bases (amines), such as piperazinium chloride, methyl piperazinium chloride, and ethylene diamine dihydrochloride. One example of a preferred buffer is Tris-Cl. Enough additional base must be added to adjust the diluted buffer acid to the desired pH, between 4 and 9. If it is desired to omit all chloride ion from the solvent, equivalent buffering can be obtained by combining the basic amine (e.g., piperazine or ethylene diamine) with enough of the acid used to prepare the eluting salt in order to attain the desired pH value.

In the practice of the invention, partially denaturing conditions can be obtained by using lower pH values in the mobile phase. Lower pH adds positive charges onto A, G, and C bases. Higher pH values, such as greater than about pH 9–10, can be used to partially denature double stranded DNA. The anion-exchange separation is preferably performed on a matrix carrying quaternary amine functional groups when the pH value is above about 10. When using a mobile phase having a pH above 9, the anion-exchange solid having silica backbone should be avoided since the solid tends to dissolve a this pH.

The anion-exchange solvents of the present invention also may contain additives, such as chelating agents at low concentrations (e.g., EDTA or DTPA in the 0.1–10 mM concentration range) or organic solvents such as acetonitrile, formamide, methanol, ethanol, acetonitrile, ethyl acetate, and 2-propanol, and N-methyl pyrrolidone in the 0.1–40% concentration range. The chelator may prevent $Mg^{2+}$, commonly found in nucleic acid preparations and tightly bound to nucleic acid, from interfering with the anion-exchange separation. It may also prevent adventitious iron, a ubiquitous contaminant usually present as a complex ion of the Fe (III) oxidation state, from catalyzing nucleic acid oxidation and cleavage by dissolved $O_2$. An especially preferred chelator for blocking iron-catalyzed oxidation reactions is deferoxamine mesylate, manufactured by Ciba-Geigy and sold by Sigma Chemical Co.; an 0.1 mM concentration of this compound is adequately protective.

The chelating agent can be a coordination compound. Examples of preferred chelating agents include water soluble chelating agents and crown ethers. Non limiting example of suitable chelating agents include: acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide. α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, β-hydroxyquinaldine, β-hydroxyquinoline, 1,10-phenanthroline, picolinic acid, quinaldic acid, α,α',α'-terpyridyl, 9-methyl-2,3,7-trihydroxy-6-fluorone, pyrocatechol, rhodizonic acid, salicylaldoxime, salicylic acid, tiron, 4-chloro-1,2-dimercaptobenzene, dithiol, mercaptobenzothiazole, rubeanic acid, oxalic acid, sodium diethyidithiocarbarbamate, zinc dibenzyldithiocarbamate, deferoxamine mesylate, crown ethers, and mixtures of any one or more of the above In addition to (a) the presence of an alkylammonium eluting salt in the 0.5 to 2M concentration range and (b) buffering in the pH 4–9 range at least equivalent to that provided by 0.01M of a buffer acid with a pKa between 3.5 and 9.5, the anion-exchange solvents of the present invention must meet a third requirement: sufficient UV transparency, especially near 260 nm, to permit spectrophotometric assay of eluted nucleic acid. Absorbances at 260 nm below 0.01 (1 cm path length) relative to distilled water are preferred, absorbances between 0.01 and 0.1 can be tolerated, as long as both buffers in binary gradient elution have approximately the same absorbance. Although there is no strict absorbance cut-off, the degree to which the absorbance exceeds approximately 0.1 increasingly limits the ability to analyze very small amounts of nucleic acid. Therefore, an important part of preparing the anion-exchange solvent is the procurement of UV-transparent components and the storage of components and finished solvents under conditions which disfavor color-forming reactions, principally condensations and oxidations. Preferred conditions are darkness, low temperature, and the use of plastic containers which do not themselves leach UV-absorbing materials (principally antioxidants) into their aqueous contents. Glass containers are acceptable, preferably after soaking in strong mineral acids such as $HNO_3$ to remove absorbed oxidatively active metals such as iron. In the interest of minimizing color formation, it is preferred that the solvents of the present invention are freshly prepared, especially if they contain organic solvents. It is also preferred to restrict buffer acid concentration to 0.05M or below, preferably no more than 0.02M. If the solvent pH is between about 7 and about 4 or if a quaternary ammonium functional group is used in the anion-exchange solid, the need for pH buffering in the salt is minimal.

Several treatments of the anion-exchange solvents of the present invention are useful for removing UV-absorbing impurities and for retarding the generation of more such impurities. The UV-absorbing impurities are substantially composed of aromatic organic compounds, which can be removed by contacting the solvents with solids which preferentially adsorb such compounds. Such solids include charcoal, beaded macroreticular polystyrene-divinylbenzene resins like XAD-2, XAD-16, and XAD-4 and acrylic resins like XAD-7 and XAD-8 (Rohm and Haas), and pyrolized beaded macroreticular polystyrene-divinyl benzene resins like Ambersorb® XE-340, XE-347, and XE-348 (Rohm and Haas).

Insofar as solvent coloration (in the UV) results from oxidative side reactions during manufacture and storage, it can be reduced by adsorptive removal of the oxidatively active transition metals, principally Fe, Cr, Co, and Cu, present as impurities and responsible for catalyzing oxidation of solvent components by dissolved oxygen in the solvent. A preferred mode of removing transition-metal contaminants is to contact the solvent or the components from which it is made with a chelating solid. Commercially available chelating solids include Chelex 20 and 100 (BioRad Laboratories), Amberlite® IRC-718 (Rohm and Haas), Chelite® C, N. and P (Serva Biochemicals), Duolite ES 346, ES 466, and ES 467 (Chemical Process Co.), BioRex and Chelex Chelating Membranes (Bio-Rad Laboratories), and Chelating Sepharose Fast Flow (Pharmacia LKB Biotechnology).

Contacting solvents or their components with solids which preferentially bind aromatic compounds can be accomplished by stirring the suspended solid in the solvent or an aqueous concentrate of a component, followed by settling of the solid and decantation or filtration of the supernatant liquid. Alternatively, the solid can be packed in a cylindrical column through which the solvent or a solution of a solvent component is passed at a rate sufficiently low that complete removal of the impurity from the solvent is effected. Some adsorptive solids now are available embedded in porous plastic matrices in filter form, so that effective contacting requires only passage of the anion-exchange solvent through the filter under relatively low applied pressure.

A final useful mode of anion-exchange solvent preparation is microfiltration under vacuum or pressure through a filter of nominal pore size no greater than 0.22 µm, preferably using a sterile filter and receiver. An especially preferred filter material is the 0.02 µm pore size alumina honeycomb membrane made by Anotec Separations Limited and sold by many laboratory reagent and equipment suppliers. Such filtration not only removes particulate materials which might damage chromatographic equipment, but also extends solvent storage lifetime by removing bacteria which might metabolize solvent components.

The most important component of the HPLC equipment is the column and its packing. For analytical separations, column internal diameter preferably will not exceed 10 mm and more preferably will not exceed 5 mm; column length will preferably not exceed 150 mm and may be as short as 10 mm. A preferred packing is a 2.5 µm diameter nonporous organic polymeric (acrylic) material carrying a diethylaminoethyl functional group manufactured by the Tosoh Corporation as "DEAE-NPR", packed in 4.6×35 mm stainless steel columns, and sold by Supelco, the Nest Group, and The Perkin-Elmer Corporation. Also preferred are 2.5 µm diameter nonporous acrylic polymeric beads carrying a diethylaminoethyl functional group, manufactured and sold by the Waters Chromatography Division of Millipore Corporation as "Gen-Pak FAX", packed in 4.6×100 mm stainless steel columns. Also preferred are 8 µm diameter porous (1000 Å or 4000 Å nominal pore size) polystyrene matrices coated with a hydrophilic polymer and carrying a quaternary ammonium group, manufactured by Polymer Laboratories Limited as "PL-SAX", packed in 4.6×50 or 150 mm stainless steel columns, and sold by Polymer Laboratories, The Perkin-Elmer Corporation, and PerSeptive Biosystems. A suitable packing includes spherical particles consisting of 10 µm diameter nonporous polystyrene spheres covered with 0.2 µm nonporous polystyrene beads carrying a quaternary ammonium functional group, manufactured and sold by Dionex Corporation as "ProPac PA1" or "NucleoPac PA-100", packed in 4×50 mm plastic columns. Another packing is 7 µm diameter porous (4000 Å nominal pore size) silica materials covalently coated either with a diethylaminoethyl-bearing silane or with polyethylenimine, manufactured by Machery-Nagel as "Nucleogen 4000-7" or as "Nucleosil 4000-7", respectively, packed in 4×50 mm stainless steel columns and sold by Rainin. Least preferred are 10 µm diameter porous (400–600 Å nominal pore size) acrylic polymeric materials carrying a quaternary amine functional group, manufactured and sold by Pharmacia LKB as "Mono-Q", packed in 5×50 mm glass columns with plastic end-fittings.

The optimal separation column is designed as follows: The chromatographic resins are preferably packed, by methods well known in the chromatographic art, in cylindrical columns which have diameters between about 2 mm and 6 mm and lengths between about 10 mm and about 30 mm. These preferably have a bottom end frit, the porous part of which completely covers the bed cross-section, and a top end frit, the porous part of which covers only a fraction of the bend cross-section, centered on the column axis. For columns with 4.6 mm internal diameters, a selection of such end frits with restricted-diameter porous plugs is available from Upchurch Scientific.

Given the appropriate anion-exchange column, nucleic acid separations for mutation detection can be run on a wide range of commercially available HPLC equipment with the solvents and processes of the present invention. Preferred for the present invention is a binary gradient mobile phase delivery system, column thermostating to a precision of at least ±0.1° C., and UV spectrophotometric detection at 260 nm. However, very fast, efficient resolution of double-stranded DNA in the 50–1,000 bp size range with complete gradient separation in less than 3 minutes can be obtained on the Tosoh DEAE-NPR material if the HPLC equipment meets the following criteria: total volume between solvent mixer and column of less than 100 µL, total flow rate as high as 1.5 ml./min., detector response time below 100 ms, and detector volume below 10 µL. Additionally, it is preferred to reduce the length of tubing between column and detector to less than 2 cm and to thermostat the injector and the tubing which connects the injector to the column.

For most precise use of the anion-exchange solvents of the present invention, a modification of conventional HPLC solvent reservoirs is desirable to minimize evaporation of water and the resulting concentration of eluting salt, which will cause retention times systematically to become shorter as the reservoir is depleted. In this modification, the solvent is enclosed in a collapsible plastic bag within a more rigid reservoir shell, such that there is minimal vapor space over the liquid; the bag is tightly sealed except for the outlet to the HPLC pump. As the reservoir contents are depleted, the bag collapses to maintain minimal solvent contact with air. Preferably, the bag is made of a plastic with minimal permeability to both water and air. Also preferably, the solvent is degassed by methods well known to the chromatographic art before introduction into the bag. Then it should be possible to supply bubble-free solvent to the HPLC pumps without helium sparging, a common practice which increases the opportunity for water evaporation. Commercially available from NOW Technologies (Minneapolis, Minn.) is a 2.5 Liter high-density polyethylene reservoir containing a collapsible Teflon liner, well suited to reducing HPLC solvent evaporation, HPLC separation of nucleic acids according to the present invention is effected optimally by (a) equilibrating the column with the starting solvent composition, containing the eluting salt at a concentration between about 0.5 and about 1M, (b) injecting the nucleic acid-containing sample in a volume of about 1 µL to about 100 µL (preferably about 10 µL), (e) initiating a continuous gradient program which increases the eluting salt concentration to a value between about 1M and about 2M in an interval between about 2 min. and about 30 min., and (d) recording UV absorbance in the 260 nm region. Optionally, the effluent from the spectrophotometric detector can be collected, in either fractions of equal volume or fractions chosen to contain individual chromatographic peaks. If the elution profile, a graph of absorbance versus time or volume, is recorded digitally, in any of many commercially available microcomputers based data systems, it can be scaled optimally when the chromatographic run is complete.

A preferred method to remove dissolved oxygen in the mobile phase is the use of an inline degassing system. An example of a suitable degasser is the Degassit Model 6324.

The optimal HPLC gradient elution profile commonly is chosen by trial and error. Once the starting and final concentrations of eluting salt have been found which separate all of the peaks of interest from one another and from the commonly observed "injection spike" of UV-absorbing material which is not retained on the column, the average steepness of the gradient is chosen to effect the separation in the desired interval.

The following examples illustrate, but in no way are intended to limit the scope of the present invention.

EXAMPLE 1

General Procedure

Oligonucleotides and polynucleotides may be obtained by polymerase chain reaction (PCR). In this case, primers are selected flanking the sequence of interest and amplification of the oligonucleotide/polynucleotide of interest is carried out by standard procedures (Mullis, U.S. Pat. No. 4,683,202, issued Jul. 28, 1987; Mullis et al., U.S. Pat. No. 4,683,195, issued Jul. 28, 1987). Source nucleic acid for the oligonucleotides of interest may be RNA (Kawasaki, et al. in PCR TECHNOLOGY: PRINCIPLES AND APPLICATIONS OF DNA AMPLIFICATION (H. A. Erlich, ed.) Stockton Press (1989); Wang, et al. in PCR PROTOCOLS: A GUIDE TO METHODS AND APPLICATIONS (M. A. Innis, et al., eds.) Academic Press (1990)) or DNA.

"HOT START PCR" can be performed (D'Aquila, et al.) using standard techniques ("AMPLIWAX", Perkin-Elmer Biotechnology, Norwalk, Conn.) in order to make the PCR amplification more robust for amplification of diverse sequences, which ideally require different amplification conditions for maximal sensitivity and specificity.

PCR can also be carried out using reaction conditions that allow for the amplification of long target sequences ("rTth-XL" polymerase and "XL PCR BUFFERS", Applied Biosystems, Foster City, Calif.). The types of systems used for these "long-range" PCR reactions contain a mixture of polymerases one of which has proof-reading activity (i.e., 3' to 5' exonuclease activity) that corrects misincorporated nucleotides, an event that if uncorrected can retard further polymerization, ultimately limiting the size of sequence efficiently amplified. The exclusive use of thermostable polymerases with proof-reading activity in PCR such as Pfu I (Stratagene, La Jolla, Calif.) or ULTma (Perkin Elmer, Norwalk Conn.) yield higher fidelity PCR products and are preferred for cloning and subsequent gene expression studies.

Amplification products can be separated from excess PCR primers by a single pass through a "WIZARD PCR COLUMN" (Promega, Madison, Wis.) following the manufacturer's instructions. The "WIZARD PCR COLUMN" is a silica based resin that binds DNA in high ionic strength buffers and will release DNA in low ionic strength buffers. Alternatively, columns such as Qiagen "QIAQUICK" columns may be used. The amplified DNA is eluted from the column with 50–100 µL distilled water.

HPLC gradient-grade acetonitrile and standard chemical reagents were typically obtained from (JT Baker). High purity water used for preparing buffer solutions was obtained using a Milli-Q water system (Millipore, Milford, Mass.).

High performance liquid chromatography can be performed on a high pressure gradient HPLC system consisting of two high-precision high-pressure gradient pumps (Model S100, SYKAM, Gilching, Germany), a controller (Model S2000, SYKAM, Gilching, Germany), a column oven (Model S4110, SYKAM), with a stability of ±0.1° C., and a UV detector (Model UVIS 200, LINEAR, Fremont, Calif.). The dynamic high pressure-gradient system is fitted with a 200 µL mixing chamber and sample injection loop installed directly in the column oven.

A preferred HPLC system comprises the WAVE® DNA Fragment Analysis System (Transgenomic, Inc., San Jose, Calif.) which includes the following components from Hitachi Instruments, Inc. (San Jose, Calif.): Model L-7250 autosampler, Model L-7300 column oven, Model L-7400 detector, Model L-7100 dual piston pump. The HPLC system is fitted with an anion exchange column as described herein.

Newly-packed columns containing anion exchange media were typically equilibrated by first washing the column for at least 2 hours with 0.02M Tris-Cl at pH 8.0, in 15% acetonitrile, at a flow rate of 0.5 ml/minute and a temperature of 60° C.

The mobile phase was then adjusted over a 3 minute period to the starting conditions of the linear gradient to be used for sample separation prior to sample injection.

Conditioning times of 1–2 hours were determined to be sufficient for column equilibration, although overnight equilibration was found to be preferable for maximum column performance.

Following sample separation, the stationary phase was washed with 90%–100% Buffer B for 1–2 minutes at the gradient sampling conditions.

The rapid regeneration of the stationary phase allows fast and repetitive injections, thus providing a highly efficient and rapid analytical tool.

EXAMPLE 2

PCR Protocol to Amplify the A and G Alleles

Nucleotide position 168 within the 209 bp STS is, sY81, polymorphic in humans, and is either an adenine (A) or guanidine (G) base (Seielstad, et al.). Both the A and G forms were initially subcloned from human genomic DNA.

Plasmid A was obtained from Kramel Biotech (catalogue no. 033740, batch 2797133, Division of Transgenomic, Ltd., Cramlington, Northumberland, UK). Plasmid G was also obtained from Kramel Biotech (catalogue no. 033840, batch 2797236). Plasmid A was a pPCR-Script Amp SK(+) cloning vector (available from Stratagene, catalogue no. 211188; GenBank® database Accession no. U46017), having the A allele form of the 209 bp insert positioned at the Srf I site. Plasmid G was a pPCR-Script Amp SK(+) cloning vector (Stratagene), having the G allele form of the 209 bp insert positioned at the Srf I site.

Synthetic oligonucleotide single stranded PCR primers 209-F (SEQ ID NO:1) and 209-R (SEQ ID NO:2) were used to amplify the 209 base pair STS, sY81, from plasmid clones containing either allelic (A or G) form of the polymorphic STS.

PCR was carried out in a final volume of 100 µL and containing 1×PCR buffer (from 10×buffer, catalogue no. N808-0006, PE Applied Biosystems), 100 µM each dNTP (from stock solutions available as catalogue no. N808-0007, PE Applied Biosystems), 50 ng/reaction of plasmid (either A or G), 1 µM of each sense and antisense primer, 2.5 units/reaction of AmpliTaq Gold DNA Polymerase (catalogue no. N808-0241, PE Applied Biosystems). All reagents were purchased from PE Applied Biosystems, Foster City, Calif. The final plasmid DNA concentration was 50 ng/µL. Aerosol barrier filter pipette tips were used for the dispensing of reagents.

Primers were obtained from Operon Technologies (catalogue no. 9218-081):

SEQ ID NO:1 Sense: 5'-AGGCACTGGTCAGAATGAAG-3' 100548 pmoles were suspended in 1.0 mL TE buffer.
SEQ ID NO:2 Antisense: 5'-AATGGAAAATACAGCTCCCC-3' 141116 pmoles were suspended in 1.4 mL TE buffer.
TE Buffer (Teknova, Inc., Half Moon Bay, Calif.) contained 10 mM Tris-HCl, pH 8.0, 1 mM EDTA, pH 8.0, in 250 mL sterile solution.

The sequence of the A allele was:

SEQ ID NO: 3
AGGCACTGGTCAGAATGAAGTGAATGGCACACAGGACAAGTCCAGACCCAGGAAGGTCCAGTAACATGG

GAGAAGAACGGAAGGAGTTCTAAAATTCAGGGCTCCCTTGGGCTCCCCTGTTTAAAAATGTAGGTTTTA

TTATTATATTTCATTGTTAACAAAAGTCC<u>A</u>TGAGATCTGTGGAGGATAAAGGGGGAGCTGTATTTTCCA

TT

The sequence of the G allele was:

SEQ ID NO: 4
AGGCACTGGTCAGAATGAAGTGAATGGCACACAGGACAAGTCCAGACCCAGGAAGGTCCAGTAACATGG

GAGAAGAACGGAAGGAGTTCTAAAATTCAGGGCTCCCTTGGGCTCCCCTGTTTAAAAATGTAGGTTTTA

TTATTATATTTCATTGTTAACAAAAGTCCGTGAGATCTGTGGAGGATAAAGGGGGAGCTGTATTTTCCA

TT

PCR Conditions:

A GeneAmp PCR system 2400 Thermocycler was used. PCR amplifications were carried out using an initial "hot-start" for 12 min at 95° C. Denaturation was for 20sec at 94° C. followed by annealing at 63° C. for 1 min (with a touchdown of –0.5° C./cycle) and elongation at 72° C. for 1 min (15 cycles). This was followed by denaturation for 20 sec at 94° C. followed by annealing at 55° C. for 1 min and elongation at 72° C. for 1 min (23 cycles). Finally the PCR sample was stored in ice.

Hybridization Protocol:

The amplification products obtained from the amplification of both plasmids A and G were combined in equal molar ratios. This mixture was hybridized by denaturation at 95° C. for 4 minutes, followed by cooling to 25° C. at the rate of 0.1° C./4 sec for 30 min.

EXAMPLE 3

Mutation Detection Using DAEHPLC

This Example refers to FIGS. 2 and 3. For the G allele and A allele, a 3 μL sample of the amplification product from Example 1 was injected onto an anion-exchange HPLC column (100 mm×4.6 mm ID). The column contained diethylaminoethyl functionalized polyacrylate (Gen-PakTM Fax, part no. WAT015490, lot no. T82271, Waters Corp., Milford, Mass.). For analysis of the product of the hybridization procedure from Example 2, a 6.0 μL sample was injected. In FIGS. 2 and 3, buffer A was 20 mM Tris-Cl (pH=8.0) in 15% acetonitrile (Tris-Cl and acetontrile were from JT Baker, Phillipsburg, N.J.). Buffer B was 2M choline chloride (Lancaster, Pelham, N.H.) in Buffer A. The chromatography was monitored 260 nm using a UV detector. The column was eluted at 73° C., at a flow rate of 0.75 mL/min, with the following gradient:

| Time | % B |
|---|---|
| 0 | 50 |
| 0.1 | 50 |
| 10 | 70 |
| 10.1 | 100 |
| 13 | 100 |
| 13.1 | 50 |
| 16 | 50 |

The HPLC system (WAVE® DNA Fragment Analysis System from Transgenoic, Inc.) included the following components from Hitachi Instruments, Inc. (San Jose, Calif.): Model L-7250 autosampler, Model L-7300 column overn, Model L-7400 detector, Model L-7100 dual piston pump.

Six separate runs were performed at 72, 73, 74, 75, 76, and 77° C. to examine the effect of column temperature on denaturation and subsequent detection of a 209-mer duplex with a single base-pair mismatch. The results are shown in FIG. 2. At 76° C., complete denaturation of the duplex was observed, as evidenced by the detection of two single peaks with retention times corresponding to those of each of the single stranded oligonucleotides. At the lower temperature of 72° C., a single peak corresponding to the annealed oligonucleotides was observed.

Referring to FIG. 1, double-stranded DNA homoduplex A, "homo-A-209", was composed of two complementary 209-nucleotide fragments, polynucleotide 10 (SEQ ID NO:3) and polynucleotide 20 (SEQ ID NO:5). Double stranded DNA homoduplex G, "homo-G-209", a 209-base pair fragment identical in sequence to homo-A-209 with the exception of one base pair (a G-C substituted for A-T present in homo-A-209) was composed of polynucleotide 30 (SEQ ID NO:4) and complementary polynucleotide 40 (SEQ ID NO:6). Polynucleotide 30 was identical in sequence to polynucleotide 10, with the exception of a guanosine at position 168 from the 5' end of polynucleotide 30, in comparison to an adenosine at the analogous position in polynucleotide 10. In a similar fashion, polynucleotide 40 was identical in sequence to polynucleotide 20, with the exception of a cytosine at position 42 from the 5' end replacing a thymidine in the same position in polynucleotide 20.

SEQ ID NO: 5
AATGGAAAATACAGCTCCCCCTTTATCCTCCACAGATCTCATGGACTTTTGTTAACAATGAAATATAAT

AATAAAACCTACATTTTTAAACAGGGGAGCCCAAGGGAGCCCTGAATTTTAGAACTCCTTCCGTTCTTC

TCCCATGTTACTGGACCTTCCTGGGTCTGGACTTGTCCTGTGTGCCATTCACTTCATTCTGACCAGTGC

CT

SEQ ID NO: 6
AATGGAAAATACAGCTCCCCCTTTATCCTCCACAGATCTCACGGACTTTTGTTAACAATGAAATATAAT

AATAAAACCTACATTTTTAAACAGGGGAGCCCAAGGGAGCCCTGAATTTTAGAACTCCTTCCGTTCTTC

TCCCATGTTACTGGACCTTCCTGGGTCTGGACTTGTCCTGTGTGCCATTCACTTCATTCTGACCAGTGC

CT

The double stranded oligonucleotides homo-A-209 and homo-G-209 were subjected to denaturation and reannealing under the conditions described in Example 2. A schematic representation of the products formed by denaturing the above 209-mer homoduplexes followed by reannealing is provided in FIG. 1. The resulting mixture of products, containing original homoduplexes homo-A-209 and homo-G-209 and newly formed heteroduplexes hetero-AC-209 and hetero-GT-209 were then analyzed by DAEHPLC. Hetero-AC-209 represents the double stranded product formed by annealing polynucleotides 10 and 40, and contains a single base pair A-C mismatch at position 168. Hetero-GT-209 represents the double stranded product formed by annealing polynucleotides 20 and 30, and contains a single base pair G-T mismatch at position 168.

Samples of each of homo-A-209, homo-G-209, and the resulting heteroduplexes formed by denaturation and naturation of homo-A-209 and homo-G-209, were directly chromatographed as shown in FIG. 3 as chromatographs 22, 24, 28, respectively. Chromatograph 26 is from a mixture of homo-A-209 and homo-G-209 combined as described in Example 2, but not subjected to the hybridization procedure.

At a less stringent column temperature of 72° C., separation/detection of the product mixture containing homo-A-209, homo-G-209, hetero AC-209, and hetero-GT-209 was not achieved (FIG. 2). However, upon raising the column temperature to 73° C., the two homoduplex products were clearly separated from the heteroduplexes, which eluted from the column slightly later than did the homoduplexes.

At 73° C., the DNA fragments are only partially denatured using the optimized chromatographic conditions of the present invention, resulting in the formation of a "bubble" at the site of the base-pair mismatch. Without wishing to be bound by any particular theory, this partial denaturation or bubble causes a shift towards longer retention times and allows the separation of heteroduplexes containing a single base pair mismatch from homoduplexes of the same size, as illustrated in FIG. 2.

In summary, the above results show the effective separation of larger nucleic acid duplexes (e.g. over 200 base pairs) containing a single base pair mismatch from homoduplexes of about the same size by partial denaturation of the heteroduplexes using the DAEHPLC conditions described herein, leading to longer retention times.

EXAMPLE 4

Anion-Exchange HPLC Separation of Double-Stranded DNA with NaCl as Eluting Salt

A double-stranded DNA sample containing a mixture of homoduplex and heteroduplex molecules is prepared as described in Example 2 and analyzed by anion-exchange HPLC under conditions similar to those described in U.S. Pat. No. 5,866,429. The HPLC mobile phase buffers are the following: Buffer A contains 10 mM cyclohexylaminoethane sulfonic acid (CHES, pKa 9.50 at 25° C.), 500 mM NaCl, pH 8.99; Buffer B contains 10 mM CHES, 700 mM NaCl, pH 8.77. The HPLC equipment consists of the following: dual Gilson model 302 pumps with 10 WSC heads, a Gilson model 811 dynamic mixer with a 65 µL mixing chamber, a Gilson model 802B manometric module, a Gilson model 231 sample injector with a 50 µL loop, a column heater from Jones Chromatography Ltd., a Perkin-Elmer model LC-95 UVNisible spectrophotometer detector with an 8 µL (10 mm path) flow cell and a 20 ms response-time setting, a Gilson model 621 data module, controlled and monitored by Gilson model 715 controller software (version 1.0) in a PC-AT clone. Column temperature is measured to ±0.1° C. with a Physitemp model BAT-1 2 electric thermometer monitoring a teflon-coated 1/20 inch diameter type T thermocouple taped to the column body.

The anion-exchange HPLC column is a Tosoh DEAE-NPR column, 4.6×35 mm, supplied by Supelco or The Perkin-Elmer Corporation. The following solvent gradient program is applied at 1.0 mL/min total flow rate (time from injection, with all gradient segments linear): 8% buffer B (0.516M NaCl) at 0 time 27% buffer B (0.554M NaCl) at 0.30 min.; 50% buffer B (0.600M NaCl) at 1.30 min.; 50% buffer B at 1.60 min.; 100% buffer B (0.700M NaCl) at 1.70 min.; 100% buffer B at 2.10 min.; 8% buffer B at 2.20 minutes.

A series of injections of 6 µL of the DNA mixture are made at temperatures in the range of 50° C. to 80° C. The results show the effect of temperature on the elution profile and the appearance of multiple peaks as the temperature is increased.

EXAMPLE 5

Anion-Exchange HPLC Separation of Double-Stranded DNA with Sodium Chloride Salt and Organic Solvent The analysis in Example 4 is repeated but the mobile phase buffers each include 15% by volume acetonitrile.

EXAMPLE 6

Anion-Exchange HPLC Separation of Double-Stranded DNA with Tetramethylammonium Chloride as Eluting Salt The DNA sample, HPLC equipment, HPLC column, HPLC flow rate, spectrophotometer detector settings, and general experimental design are as described in Example 4. The HPLC solvents are the following: Buffer A contains 10 mM 2(N-morpholino) ethane sulfonic acid (MES, pKa= 6.15° C. at 20° C.) 800 mM tetramethylammonium chloride (TMAC), pH 6.05; Buffer B contains 10 mM MES, 1500 mM TMAC, pH 6.04. The following gradient program is used, all gradient segments being linear. 12% buffer B (0.884M TMAC) at 0 time; 35% buffer B (1.045M TMAC) at 1.00 min.; 45% buffer B (1.115M TMAC) at 3.00 min.; 100% buffer B at 3.10 min.; 100% buffer B at 3.60 min.; 12% buffer B at 3.70 min.

A series of injections of 6 μL of the hybridized DNA mixture from Example 2 are made at temperatures in the range of 50° C. to 80° C. The results show the effect of temperature on the elution profile and the appearance of multiple peaks as the temperature is increased.

EXAMPLE 7

Anion-Exchange HPLC Separation of Double-Stranded DNA with Tetramethylammonium Chloride Salt and Organic Solvent The analysis in Example 6 is repeated but the mobile phase buffers each include 15% by volume acetonitrile.

Resolution can be improved by such remedies as (a) adjusting HPLC flow rate (e.g., from 1.0 to 1.5 mL/min), (b) minimizing the length and diameter of the tubing which connects the column to the detector, (c) modifying column dimensions to reduce the length/diameter ratio and the total length, and (2) using an column inlet frit with a smaller diameter than the column diameter to minimize dead space at the top of the column.

EXAMPLE 8

Anion-Exchange HPLC Separation of Double-Stranded DNA with Tetramethylammonium Formate (TMAF) as Eluting Salt The DNA sample, HPLC equipment, HPLC column, HPLC flow rate, spectrophotometer detector settings, and general experimental design are as described in Example 4. The HPLC solvents are the following. Buffer A contains 20 mM cyclohexylaminoethane sulfonic acid (CHES) 1.0M TMAF, pH 9.0. Buffer B contains 20 mM CHES 1.5M TMAF, pH 9.0. The buffers are prepared by adding tetramethylammonium hydroxide to solutions of formic acid plus CHES until pH 9.0 is reached and then adding a small amount of water to reach a final volume containing 20 mM CHES and 1.0 or 1.5M formate. All buffers are vacuum filtered through an Anotec membrane with 0.02 μm pore size (Whatman, Inc., Clifton, N.J.). The following gradient program is used, all gradient segments being linear: 6.5% Buffer B at 0.2 min; 6.5% at 0 min; 12.8% at 0.2 min; 18.2% at 0.4 min; 22.8% at 0.6 min; 26.5% at 0.8 min; 29.3% at 1.0 min; 32.0% at 1.2 min; 34.5% at 1.4 min; 37.0% at 1.6 min; 39.4% at 1.8 min; 41.7% Buffer B at 2.0 min; 6.5% at 2.2 min [next injection scheduled at 3.0 min].

A series of injections of 6 μL of the hybridized DNA mixture from Example 2 are made at temperatures in the range of 50° C. to 80° C. The results show the effect of temperature on the elution profile and the appearance of multiple peaks as the temperature is increased.

EXAMPLE 9

Anion-Exchange HPLC Separation of Double-Stranded DNA with Tetramethylammonium Formate (TMAF) Salt and Organic Solvent The analysis in Example 8 is repeated but the mobile phase buffers each include 15% by volume acetonitrile.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claimed is:

1. A chromatographic method for separating heteroduplex and homoduplex DNA molecules in a mixture, said method comprising:
   (a) applying the mixture to an anion-exchange solid;
   (b) eluting the solid of step (a) with a mobile phase comprising an eluting salt, an organic solvent, and a buffer, wherein said eluting is carried out under conditions effective to at least partially denature said heteroduplexes and wherein the eluting results in the separation of said heteroduplexes from said homoduplexes.

2. A method of claim 1 wherein step (b) includes contacting the solid of step (a) with a mobile phase possessing a pH in the range of 4 to 9, said mobile phase comprising:
   an eluting salt composed of equal concentrations of:
      a cation selected from the group consisting of dialkylammonium, trialkylammonium and tetraalkylammonium, or mixtures thereof, wherein the alkyl groups consist of any combination of methyl and ethyl; and
      an anion selected from the group consisting of bromide, chloride, acetate, formate, nitrate, perchlorate, dihydrogen phosphate, ethane sulfonate and methane sulfonate or mixtures thereof;
   a buffer acid with a pKa in the approximate range of 3.5 to 9.5;
   an organic solvent;
   wherein the concentration of eluting salt is systematically increased from approximately 0.5M to approximately 2.0M.

3. A method of claim 2 wherein the eluting salt is systematically increased from approximately 1.0M to approximately 2.0M.

4. A method of claim 2 wherein said cation is selected from the group consisting of dialkylammonium, trialkylammonium and tetraalkylammonium, wherein the alkyl groups consist of any combination of methyl and ethyl.

5. A chromatographic method for separating heteroduplex and homoduplex DNA molecules in a mixture, said method comprising:
   (a) applying the mixture to an anion-exchange solid;
   (b) eluting the solid of step (a) with a mobile phase comprising an eluting salt, an organic solvent, and a buffer, and contacting the solid of step (a) with a mobile phase possessing a pH in the range of 4 to 9 said mobile phase comprising an eluting salt composed of equal concentrations of a cation selected from the group consisting of dialkylammonium, trialkylammonium and tetraalkylammonium, or mixtures thereof, wherein the alkyl groups consist of any combination of methyl and ethyl and an anion selected from the group consisting of bromide, chloride, acetate, formate, nitrate, perchlorate, dihydrogen phosphate, ethane sulfonate and methane sulfonate or mixtures thereof;
   a buffer acid with a pKa in the approximate range of 3.5 to 9.5; and
   an organic solvent:
      wherein the concentration of eluting salt is systematically increased from approximately 0.5 M to approximately 2.0 M, and wherein said eluting is carried out under conditions effective to at least partially denature said heteroduplexes and wherein the eluting results in the separation of said heteroduplexes from said homoduplexes and wherein said cation comprises choline.

6. A method of claim 2 wherein said cation comprises guanidinium.

7. A method of claim 2 where said cation comprises sodium.

8. A method of claim 2 wherein said anion is formate or chloride.

9. A method of claim 2 wherein said mobile phase includes a metal chelating agent.

10. A method of claim 9 wherein said metal chelating agent is selected from the group consisting of acetylacetone, alizarin, aluminon, chloranilic acid, kojic acid, morin, rhodizonic acid, thionalide, thiourea, nioxime, salicylaldoxime, dimethylglyoxime, α-furildioxime, cupferron, α-nitroso-β-napthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, β-hydroxyquinaldine, β-hydroxyquinoline, 1,10-phenanthroline, picolinic acid, quinaldic acid, α, α', α"-terpyridyl, 9-methyl-2,3,7-trihydroxy-6-fluorone, pyrocatechol, rhodizonic acid, salicylaldoxime, salicylic acid, tiron, 4-chloro-1,2-dimercaptobenzene, dithiol, mercaptobenzothiazole, rubeanic acid, oxalic acid, sodium diethyldithiocarbarbamate, zinc, dibenzyldithiocarbamate, deferoxamine mesylate, crown ethers, and mixtures of any one or more of the above.

11. A method of claim 1, wherein said solid is comprised of a silica, polysaccharide or synthetic polyolefin backbone.

12. A method of claim 11 wherein said polyolefin is a polystyrene or polyacrylic.

13. A method of claim 1, wherein said solid comprises a polyacrylic backbone.

14. A method of claim 1, wherein said solid comprises diethylaminoethyl functional groups.

15. A method of claim 1, wherein said solid comprises polyethyleneimine functional groups.

16. A method of claim 1, wherein said solid comprises particles with an average diameter between approximately 2 micron and 10 micron.

17. A method of claim 1, wherein the solid is substantially nonporous.

18. A method of claim 1, wherein said solid comprises a polystyrene backbone.

19. A method of claim 1, wherein said mobile phase contains an organic solvent selected from the group consisting of methanol, ethanol, acetonitrile, ethyl acetate, formamide, 2-propanol, and N-methyl pyrrolidone.

20. A method of claim 1 wherein said mobile phase contains less than about 40% by volume of said organic solvent.

21. A method of claim 1 wherein said eluting is carried out at a column temperature greater than about 50° C.

22. A method of claim 1 wherein said eluting is carried out at a column temperature between about 40° C. and about 80° C.

23. A method of claim 1 wherein the concentration of said eluting salt is continuously increased.

24. A method of claim 1 including analyzing the mobile phase after the elution step (b) for the concentration of said DNA molecules.

25. A method of claim 24 wherein the concentration of said DNA molecules is measured by ultraviolet absorbance in the approximate wavelength range of about 250 nm to about 290 nm.

26. A method of claim 1 wherein the total time required to complete said method is between about 2 minutes and about 30 minutes.

27. A method of claim 1 wherein the concentration of organic solvent is systematically increased.

28. A method of claim 1 where said solid is contained in a column of cylindrical geometry.

29. A chromatographic method for separating heteroduplex and homoduplex DNA molecules in a mixture, comprising:
(a) applying the mixture to an anion-exchange solid,
(b) eluting the solid of step (a) with a mobile phase containing an eluting salt and a buffer, where said eluting is carried out under conditions effective to at least partially denature said heteroduplexes and where the eluting results in the separation of said heteroduplexes from said homoduplexes.

30. A method of claim 29, wherein step (b) includes contacting the solid of step (a) with a mobile phase possessing a pH in the range of 4 to 9 comprising:
an eluting salt composed of equal concentrations of:
a cation selected from the group consisting of dialkylammonium, trialkylammonium and tetraalkylammonium, wherein the alkyl groups consist of any combination of methyl and ethyl;
an anion selected from the group consisting of bromide, chloride, acetate, formate, nitrate, perchlorate, dihydrogen phosphate, ethane sulfonate and methane sulfonate; and
a buffer acid with a pKa in the approximate range of 3.5 to 9.5;
wherein the concentration of eluting salt is systematically increased from approximately 0.5M to approximately 2.0M.

31. A chromatographic method for separating heteroduplex and homoduplex DNA molecules in a mixture comprising:
(a) applying the mixture to an anion-exchange solid, and
(b) eluting the solid of step (a) with a mobile phase containing an eluting salt and a buffer, where said eluting is carried out under conditions effective to at least partially denature said heteroduplexes and where the eluting results in the separation of said heteroduplexes from said homoduplexes and further solid of step (a) with a mobile phase possessing a pH in the range of 4 to 9 comprising:
an eluting salt composed of equal concentrations of a cation selected from the group consisting of dialkylammonium, trialkylammonium, and tetraalkylammonium wherein the alkyl groups consist of any combination of methyl and ethyl;
an anion selected from the group consisting of bromide, chloride, acetate, formate, nitrate, perchlorate, dihydrogen phosphate, ethane sulfonate, and methane sulfonate; and
a buffer acid with a pKa in the approximate range of 3.5 to 9.5; wherein the concentration of eluting salt is systematically increased from approximately 0.5 M to approximately 2.0 M and wherein said cation comprises choline.

32. A method of claim 30 wherein said cation comprises sodium.

33. A method of claim 30 wherein said mobile phase includes a metal chelating agent.

34. A method of claim 33 wherein said metal chelating agent is selected from the group consisting of acetylacetone, alizarin, aluminon, chloranilic acid, kojic acid, morin, rhodizonic acid, thionalide, thiourea, nioxime, salicylaldoxime, dimethylglyoxime, α-furildioxime, cupferron, α-nitroso-β-napthol, nitros-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, β-hydroxyquinaldine, β-hydroxyquinoline, 1,10-phenanthroline, picolinic acid, quinaldic acid, α, α', α"-terpyridyl, 9-methyl-2,3,7-trihydroxy-6-fluorone, pyrocatechol, rhodizonic acid, salicylaldoxime, salicylic acid, tiron, 4-chloro-1,2-dimercaptobenzene, dithiol, mercaptobenzothiazole, rubeanic acid, oxalic acid, sodium diethyldithiocarbamate, zinc dibenzyldithiocarbamate, deferoxamine mesylate, crown ethers, and mixtures of any one or more of the above.

35. A method of claim 30 wherein said cation comprises guanidinium.

36. A method of claim 30 wherein said anion is formate or chloride.

37. A method of claim 30 wherein the eluting salt is systematically increased from approximately 1.0M to approximate 2.0M.

38. A method of claim 30 including analyzing the mobile phase eluting from the column for the presence of DNA.

39. A method of claim 30 wherein said eluting is carried out at a column temperature greater than about 50° C.

40. A method of claim 30 wherein said eluting is carried out at a column temperature between about 40° C. and about 80° C.

41. A chromatographic method for separating heteroduplex and homoduplex DNA molecules in a mixture, said method comprising:
(a) applying the mixture to an anion-exchange solid;
(b) eluting the solid of step (a) with a mobile phase containing an eluting salt, an organic solvent, and a buffer, wherein said eluting is carried out under conditions effective to at least partially denature said heteroduplexes and wherein the eluting results in the separation of said heteroduplexes from said homoduplexes;
wherein step (b) includes contacting the solid of step (a) with a mobile phase possessing a pH in the range of 4 to 9 comprising:
an eluting salt comprising of equal concentrations of:
a cation;
an anion;
a buffer acid with a pKa in the approximate range of 3.5 to 9.5; and an organic solvent;

wherein said mobile phase contains less than about 40% by volume of said organic solvent;

wherein the concentration of eluting salt is systematically increased from approximately 0.5M to approximately 2.0M.

42. A chromatographic method for separating heteroduplex and homoduplex DNA molecules in a mixture, comprising:

(a) applying the mixture to an anion-exchange solid;

(b) eluting the solid of step (a) with a mobile phase comprising an eluting salt, an organic solvent, and a buffer, wherein said eluting is carried out under conditions effective to at least partially denature said heteroduplexes and wherein the eluting results in the separation of said heteroduplexes from said homoduplexes;

wherein step (b) includes contacting the solid of step (a) with a mobile phase possessing a pH in the range of 4 to 9 comprising an eluting salt comprising:

betaine at a concentration in the range of about 0.5M to about 6M;

a buffer acid with a pKa in the approximate range of 3.5 to 9.5; and, an organic solvent;

wherein said mobile phase contains less than about 40% by volume of said organic solvent;

wherein the concentration of eluting salt is systematically increased from approximately 0.5M to approximately 2.0M.

43. A method of claim 42 wherein the eluting is carried out at a column temperature greater than about 50° C.

44. A chromatographic method for separating heteroduplex and homoduplex DNA molecules in a mixture, said method comprising:

(a) applying the mixture to an anion-exchange solid, (b) eluting the solid of step (a) with a mobile phase containing an eluting salt, an organic solvent, and a buffer, where said eluting is carried out under conditions effective to at least partially denature said heteroduplexes and where the eluting results in the separation of said heteroduplexes from said homoduplexes;

wherein step (b) includes contacting the solid of step (a) with a mobile phase possessing a pH in the range of 4 to 9 comprising:

an eluting salt comprising equal concentrations of:

a cation;

an anion;

a buffer acid with a pKa in the approximate range of 3.5 to 9.5; and wherein the eluting is carried out at a column temperature greater than about 50° C., wherein the concentration of eluting salt is systematically increased from approximately 0.5M to approximately 2.0M.

45. The method of claim 1, where prior to said applying step the DNA molecules are amplified using the polymerase chain reaction and the amplified DNA molecules are denatured and renatured to form a mixture of heteroduplex and homoduplex DNA molecules.

* * * * *